US012761974B2

(12) United States Patent
Mushtaq et al.

(10) Patent No.: US 12,761,974 B2
(45) Date of Patent: Oct. 13, 2026

(54) BED SYSTEM WITH EDGE-BASED AND REMOTE-COMPUTING BASED MODEL DEPLOYMENT FOR DETERMINING USER HEALTH METRICS

(71) Applicant: SNBR INC., Minneapolis, MN (US)

(72) Inventors: Faisal Mushtaq, San Diego, CA (US); Sajeev Mayandi, Minneapolis, MN (US)

(73) Assignee: SNBR Inc., Minneapolis, MN (US)

(*) Notice: Subject to any disclaimer, the term of this patent is extended or adjusted under 35 U.S.C. 154(b) by 321 days.

(21) Appl. No.: 18/437,909

(22) Filed: Feb. 9, 2024

(65) Prior Publication Data

US 2024/0268763 A1 Aug. 15, 2024

Related U.S. Application Data

(60) Provisional application No. 63/444,666, filed on Feb. 10, 2023.

(51) Int. Cl.
*G06F 9/50* (2006.01)
*A61B 5/00* (2006.01)
(Continued)

(52) U.S. Cl.
CPC .......... *G06F 9/5072* (2013.01); *A61B 5/0022* (2013.01); *A61B 5/02055* (2013.01);
(Continued)

(58) Field of Classification Search
CPC ........ G06F 9/50; G06F 9/5061; G06F 9/5072; G06F 9/48; G06F 9/54
See application file for complete search history.

(56) References Cited

U.S. PATENT DOCUMENTS 4,766,628 A 8/1988 Greer et al.
4,788,729 A 12/1988 Greer et al.
(Continued)

FOREIGN PATENT DOCUMENTS

CN 103300819 9/2013
CN 105517464 4/2016
(Continued)

OTHER PUBLICATIONS

Abdellatif et al, "Edge Computing for Smart Health: Context-Aware Approaches, Opportunities, and Challenges", Special Section on Smart Caching, Communications, Computing and Cybersecurity for Information-Centric Internet of Things, Dec. 2018, IEEE, (Year: 2018).*
(Continued)

*Primary Examiner* — Charles M Swift
(74) *Attorney, Agent, or Firm* — Norton Rose Fulbright US LLP

(57) ABSTRACT

Disclosed are techniques for generating sleeper information based on user data collected at a bed system. A system can include an edge computing device, service-providing servers, and a cloud-based computing system. The servers can execute models for determining particular sleeper information based on sensor signals generated by bed sensors. A first subset of servers run in a cloud-based system and a second subset run at the edge computing device. The cloud-based computing system can receive the sensor signals, receive a request to execute a model having a relationship with a server, wrap the model with model data, transmit the wrapped model and data to the server for execution, receive model output once the wrapped model is executed, and generate at least one health metric about a user of the bed system based on correlating the model output with other model outputs or other data about the user.

20 Claims, 17 Drawing Sheets

(51) Int. Cl.

| | |
|---|---|
| ***A61B 5/0205*** | (2006.01) |
| ***G06F 9/48*** | (2006.01) |
| ***G06F 9/54*** | (2006.01) |
| ***G06N 20/00*** | (2019.01) |
| ***G16H 40/67*** | (2018.01) |

(52) U.S. Cl.

CPC .......... *A61B 5/4815* (2013.01); *A61B 5/6892* (2013.01); *A61B 5/7246* (2013.01); *A61B 5/7267* (2013.01); *G06F 9/48* (2013.01); *G06F 9/50* (2013.01); *G06F 9/5061* (2013.01); *G06F 9/54* (2013.01); *G06N 20/00* (2019.01); *G16H 40/67* (2018.01); *A61B 2562/0204* (2013.01); *A61B 2562/0247* (2013.01); *A61B 2562/0252* (2013.01)

(56) References Cited

U.S. PATENT DOCUMENTS

| | | | |
|---|---|---|---|
| D300,194 | S | 3/1989 | Walker |
| 4,829,616 | A | 5/1989 | Walker |
| 4,890,344 | A | 1/1990 | Walker |
| 4,897,890 | A | 2/1990 | Walker |
| 4,908,895 | A | 3/1990 | Walker |
| D313,973 | S | 1/1991 | Walker |
| 4,991,244 | A | 2/1991 | Walker |
| 5,144,706 | A | 9/1992 | Walker et al. |
| 5,170,522 | A | 12/1992 | Walker |
| D368,475 | S | 4/1996 | Scott |
| 5,509,154 | A | 4/1996 | Shafer et al. |
| 5,564,140 | A | 10/1996 | Shoenhair et al. |
| 5,642,546 | A | 7/1997 | Shoenhair |
| 5,652,484 | A | 7/1997 | Shafer et al. |
| 5,765,246 | A | 6/1998 | Shoenhair |
| 5,903,941 | A | 5/1999 | Shafer et al. |
| 5,904,172 | A | 5/1999 | Gifft et al. |
| 6,037,723 | A | 3/2000 | Shafer et al. |
| 6,108,844 | A | 8/2000 | Kraft et al. |
| 6,161,231 | A | 12/2000 | Kraft et al. |
| 6,202,239 | B1 | 3/2001 | Ward et al. |
| 6,397,419 | B1 | 6/2002 | Mechache |
| 6,483,264 | B1 | 11/2002 | Shafer et al. |
| 6,686,711 | B2 | 2/2004 | Rose et al. |
| 6,708,357 | B2 | 3/2004 | Gaboury et al. |
| 6,763,541 | B2 | 7/2004 | Mahoney et al. |
| 6,804,848 | B1 | 10/2004 | Rose |
| 6,832,397 | B2 | 12/2004 | Gaboury |
| D502,929 | S | 3/2005 | Copeland et al. |
| 6,883,191 | B2 | 4/2005 | Gaboury et al. |
| 7,389,554 | B1 | 6/2008 | Rose |
| 7,542,959 | B2 | 6/2009 | Barnhill et al. |
| 7,865,988 | B2 | 1/2011 | Koughan et al. |
| 8,287,452 | B2 | 10/2012 | Rifredi et al. |
| 8,336,369 | B2 | 12/2012 | Mahoney |
| 8,444,558 | B2 | 5/2013 | Young et al. |
| D691,118 | S | 10/2013 | Ingham et al. |
| D697,874 | S | 1/2014 | Stusynski et al. |
| D698,338 | S | 1/2014 | Ingham |
| D701,536 | S | 3/2014 | Sakal |
| 8,672,853 | B2 | 3/2014 | Young |
| 8,769,747 | B2 | 7/2014 | Mahoney et al. |
| 8,893,339 | B2 | 11/2014 | Fleury |
| 8,931,329 | B2 | 1/2015 | Mahoney et al. |
| 8,966,689 | B2 | 3/2015 | McGuire et al. |
| 8,973,183 | B1 | 3/2015 | Palashewski et al. |
| 8,984,687 | B2 | 3/2015 | Stusynski et al. |
| D737,250 | S | 8/2015 | Ingham et al. |
| 9,131,781 | B2 | 9/2015 | Zaiss et al. |
| 9,324,022 | B2 | 4/2016 | Williams, Jr. et al. |
| 9,370,457 | B2 | 6/2016 | Nunn et al. |
| 9,392,879 | B2 | 7/2016 | Nunn et al. |
| 9,510,688 | B2 | 12/2016 | Nunn et al. |
| 9,635,953 | B2 | 5/2017 | Nunn et al. |
| 9,706,957 | B2 | 7/2017 | Wu et al. |
| 9,730,524 | B2 | 8/2017 | Chen et al. |
| 9,737,154 | B2 | 8/2017 | Mahoney et al. |
| 9,770,114 | B2 | 9/2017 | Brosnan et al. |
| D809,843 | S | 2/2018 | Keeley et al. |
| D812,393 | S | 3/2018 | Karschnik et al. |
| 9,924,813 | B1 | 3/2018 | Basten et al. |
| 9,974,454 | B2 | 5/2018 | Sharma et al. |
| 10,058,467 | B2 | 8/2018 | Stusynski et al. |
| 10,092,242 | B2 | 10/2018 | Nunn et al. |
| 10,143,312 | B2 | 12/2018 | Brosnan et al. |
| 10,149,549 | B2 | 12/2018 | Erko et al. |
| 10,182,661 | B2 | 1/2019 | Nunn et al. |
| 10,194,752 | B2 | 2/2019 | Zaiss et al. |
| 10,194,753 | B2 | 2/2019 | Fleury et al. |
| 10,201,234 | B2 | 2/2019 | Nunn et al. |
| 10,251,490 | B2 | 4/2019 | Nunn et al. |
| 10,342,358 | B1 | 7/2019 | Palashewski et al. |
| 10,423,861 | B2 | 9/2019 | Gao et al. |
| 10,460,255 | B2 | 10/2019 | Nagaraju et al. |
| 10,729,253 | B1 | 8/2020 | Gaunt |
| 10,929,708 | B2 | 2/2021 | Syeda-Mahmood et al. |
| D932,808 | S | 10/2021 | Keeley |
| 11,347,970 | B2 | 5/2022 | Anghel et al. |
| 11,423,301 | B2 | 8/2022 | O'Shea |
| 11,450,117 | B2 | 9/2022 | Goel et al. |
| 11,699,086 | B1 | 7/2023 | O'Shea et al. |
| 11,991,658 | B2 | 5/2024 | O'Shea et al. |
| 2005/0190065 | A1 | 9/2005 | Ronnholm et al. |
| 2008/0077020 | A1 | 3/2008 | Young et al. |
| 2011/0010014 | A1 | 1/2011 | Oexman et al. |
| 2011/0115635 | A1 | 5/2011 | Petrovski et al. |
| 2011/0144455 | A1 | 6/2011 | Young et al. |
| 2012/0138067 | A1 | 6/2012 | Rawls-Meehan |
| 2013/0245502 | A1 | 9/2013 | Lange et al. |
| 2014/0250597 | A1 | 9/2014 | Chen et al. |
| 2014/0259417 | A1 | 9/2014 | Nunn et al. |
| 2014/0259418 | A1 | 9/2014 | Nunn et al. |
| 2014/0277822 | A1 | 9/2014 | Nunn et al. |
| 2015/0007393 | A1 | 1/2015 | Palashewski |
| 2015/0025327 | A1 | 1/2015 | Young et al. |
| 2015/0137994 | A1 | 5/2015 | Rahman et al. |
| 2015/0182397 | A1 | 7/2015 | Palashewski et al. |
| 2015/0182399 | A1 | 7/2015 | Palashewski et al. |
| 2015/0182418 | A1 | 7/2015 | Zaiss |
| 2015/0199919 | A1 | 7/2015 | Ander et al. |
| 2015/0310862 | A1 | 10/2015 | Dauphin et al. |
| 2015/0324690 | A1 | 11/2015 | Chilimbi et al. |
| 2016/0015314 | A1 | 1/2016 | Dusanter et al. |
| 2016/0100696 | A1 | 4/2016 | Palashewski et al. |
| 2016/0242562 | A1 | 8/2016 | Karschnik et al. |
| 2016/0300252 | A1 | 10/2016 | Frank et al. |
| 2016/0338871 | A1 | 11/2016 | Nunn et al. |
| 2016/0367039 | A1 | 12/2016 | Young et al. |
| 2017/0003666 | A1 | 1/2017 | Nunn et al. |
| 2017/0049243 | A1 | 2/2017 | Nunn et al. |
| 2017/0055896 | A1 | 3/2017 | Al-Ali et al. |
| 2017/0191516 | A1 | 7/2017 | Griffith et al. |
| 2017/0303697 | A1 | 10/2017 | Chen et al. |
| 2017/0318980 | A1 | 11/2017 | Mahoney et al. |
| 2017/0354268 | A1 | 12/2017 | Brosnan et al. |
| 2018/0116415 | A1 | 5/2018 | Karschnik et al. |
| 2018/0116418 | A1 | 5/2018 | Shakal et al. |
| 2018/0116419 | A1 | 5/2018 | Shakal et al. |
| 2018/0116420 | A1 | 5/2018 | Shakal |
| 2018/0119686 | A1 | 5/2018 | Shakal et al. |
| 2018/0125259 | A1 | 5/2018 | Peterson et al. |
| 2018/0125260 | A1 | 5/2018 | Peterson et al. |
| 2018/0341876 | A1 | 11/2018 | Ghosh et al. |
| 2018/0373988 | A1 | 12/2018 | Dhanyamraju et al. |
| 2019/0036716 | A1 | 1/2019 | Kasaragod et al. |
| 2019/0059603 | A1 | 2/2019 | Griffith et al. |
| 2019/0082855 | A1 | 3/2019 | Brosnan et al. |
| 2019/0104858 | A1 | 4/2019 | Erko et al. |
| 2019/0125095 | A1 | 5/2019 | Nunn et al. |
| 2019/0125097 | A1 | 5/2019 | Nunn et al. |
| 2019/0201265 | A1 | 7/2019 | Sayadi et al. |
| 2019/0201267 | A1 | 7/2019 | Demirli et al. |
| 2019/0201269 | A1 | 7/2019 | Sayadi et al. |
| 2019/0201270 | A1 | 7/2019 | Sayadi et al. |
| 2019/0206416 | A1 | 7/2019 | Demirli et al. |

(56) References Cited

U.S. PATENT DOCUMENTS

| | | | | |
|---|---|---|---|---|
| 2019/0209405 | A1 | 7/2019 | Sayadi et al. | |
| 2019/0279745 | A1 | 9/2019 | Sayadi et al. | |
| 2020/0019882 | A1 | 1/2020 | Garg et al. | |
| 2020/0146910 | A1 | 5/2020 | Demirli et al. | |
| 2020/0327371 | A1 | 10/2020 | Sharma et al. | |
| 2020/0364625 | A1 | 11/2020 | Baker et al. | |
| 2020/0387807 | A1 | 12/2020 | Stassen et al. | |
| 2021/0022667 | A1 | 1/2021 | Siyahjani et al. | |
| 2021/0133620 | A1 | 5/2021 | Frank et al. | |
| 2021/0225510 | A1* | 7/2021 | Yang | G16H 50/30 |
| 2021/0390003 | A1* | 12/2021 | Aghajanyan | G06F 16/22 |
| 2022/0133164 | A1 | 5/2022 | Mushtaq et al. | |
| 2022/0175600 | A1 | 6/2022 | Molina et al. | |
| 2022/0265223 | A1 | 8/2022 | Molina | |
| 2022/0323001 | A1 | 10/2022 | Nunn et al. | |
| 2023/0046169 | A1 | 2/2023 | Molina et al. | |
| 2023/0115150 | A1 | 4/2023 | Demirli et al. | |
| 2023/0190183 | A1 | 6/2023 | Molina et al. | |
| 2023/0218225 | A1 | 7/2023 | Mushtaq et al. | |
| 2023/0225517 | A1 | 7/2023 | Sayadi et al. | |
| 2023/0240922 | A1 | 8/2023 | Rao et al. | |
| 2023/0329583 | A1 | 10/2023 | Molina et al. | |
| 2023/0335239 | A1 | 10/2023 | Sayadi et al. | |
| 2023/0414178 | A1 | 12/2023 | Molina et al. | |
| 2024/0032860 | A1 | 2/2024 | Rao et al. | |
| 2024/0032861 | A1 | 2/2024 | Stusynski et al. | |
| 2024/0060815 | A1 | 2/2024 | Young et al. | |
| 2024/0065559 | A1 | 2/2024 | Molina et al. | |
| 2024/0082532 | A1 | 3/2024 | Barr et al. | |
| 2024/0105339 | A1* | 3/2024 | Matthews | G16H 50/20 |
| 2024/0115192 | A1 | 4/2024 | Sayadi et al. | |

FOREIGN PATENT DOCUMENTS

| | | |
|---|---|---|
| CN | 105595672 | 5/2016 |
| JP | 2010-099173 | 5/2010 |

OTHER PUBLICATIONS

Alabdulatif et al "Secure Edge of Things for Smart Healthcare Surveillance Framework", IEEE network, May 2019 (Year: 2019).*

U.S. Appl. No. 18/398,611, filed Dec. 18, 2023, Sayadi et al.

U.S. Appl. No. 18/417,870, filed Jan. 19, 2024, Demirli et al.

U.S. Appl. No. 18/437,909, filed Feb. 9, 2024, Mushtaq et al.

U.S. Appl. No. 18/584,517, filed Feb. 22, 2024, Garcia Molina et al.

Ben She, Yi Ming, "Data Analysis Fundamentals and Models," Dec. 2000, pp. 147-150.

* cited by examiner

BED SYSTEM WITH EDGE-BASED AND REMOTE-COMPUTING BASED MODEL DEPLOYMENT FOR DETERMINING USER HEALTH METRICS

CROSS-REFERENCE TO RELATED APPLICATIONS

This application claims the benefit of U.S. Provisional Application Ser. No. 63/444,666, filed Feb. 10, 2023. The disclosure of the prior application is considered part of the disclosure of this application, and is incorporated in its entirety into this application.

The present document relates to bed systems with automated computing techniques for determining health metrics and information for users of the bed systems.

BACKGROUND

In general, a bed is a piece of furniture used as a location to sleep or relax. Many modern beds include a soft mattress on a bed frame. The mattress may include springs, foam material, and/or an air chamber to support the weight of one or more occupants.

SUMMARY

This document generally describes systems, methods, techniques, and technology for deploying machine learning models at edge computing devices (such as bed controllers) and remote computing systems (such as cloud-based computing systems). The models can be adapted and wrapped for efficient deployment according to resource constraints that will be available where they are run at the edge computing device and/or the remote computing system. Different models for determining different user information (e.g., measures of sleep quality or determining heart rate from bed pressure signals) can be deployed at the edge computing device and the remote computing device. For example, the disclosed technology can be used to parameterize and wrap models that are then deployed at the edge computing device to efficiently generate intra-sleep health and wellness metrics and information based on real-time data collected by sensors at a bed system as a user rests on the bed. The models are wrapped so that they can be deployed in independently-run services operating at the edge computing device. The disclosed technology can also be used to parameterize and then execute models in other independently-run services operating at the remote computing system to generate inter-sleep health metrics and information for the user. The inter-sleep health metrics and information can be determined based on data collected by the sensors during one or more sleep sessions of the user and/or determinations from any of the models that are deployed on the edge.

Some embodiments described herein include a system for generating sleeper information based on user data collected at a bed system, the system having: a bed system including: at least one sensor that can be configured to generate sensor signals as a user rests on the bed system, and an edge computing device in communication over a network with other components of the bed system, a group of service-providing servers each having one or more processors and memory, the group of service-providing servers being in communication over the network with the other components of the bed system, each of the group of service-providing servers being configured to execute a model for determining particular sleeper information based at least in part on the sensor signals generated by the at least one sensor, a first subset of the group of service-providing servers running in a cloud-based system and a second subset of the group of service-providing servers running at the edge computing device, and a cloud-based computing system having one or more processors and memory. The cloud-based computing system can include: a messaging service to provide communication over the network between the cloud-based computing system, the at least one sensor, the edge computing device, and the group of service-providing servers, the messaging service being configured to: receive the generated sensor signals from the at least one sensor and transmit the received sensor signals to a data store for storage. The cloud-based computing system can include a model wrapping service to: receive, from a service-providing server amongst the group of service-providing servers via the messaging service, a request to execute a model that has a relationship with the service-providing server, retrieve, from the data store via the messaging service, the model and data for executing the model at the requesting service-providing server, the data including at least some of the sensor signals, wrap the model with the retrieved data, and transmit, via the messaging service, the wrapped model and data to the service-providing server for execution. The cloud-based computing system can also include an aggregator to: receive, from the service-providing server via the messaging service, model output once the wrapped model is executed by the service-providing server, and generate at least one health metric about the user of the bed system based on correlating the model output with at least one of (i) other model outputs or (ii) other data about the user.

Embodiments described herein can include one or more optional features. For example, the first subset of the group of service-providing servers can include an illness detection service-providing server, the illness detection service-providing server being configured to execute an illness detection model having been trained to determine, over a threshold quantity of sleep sessions of the user, whether the user developed an illness. The illness detection model can be trained to receive, as inputs, historic user health data, the generated sensor signals, and model output from one or more of the plurality of service-providing servers, process the received inputs, and generate, as a result of processing the inputs, output indicating a likelihood that the user developed the illness. The second subset of the group of service-providing servers can include: a motion detection service-providing server, a respiratory rate detection service-providing server, a heartrate detection service-providing server, a heartrate variability computation service-providing server, a time-to-fall-asleep computation service-providing server, a bed presence detection service-providing server, a snore detection service-providing server, and a snore response service-providing server. The at least one health metric can be a determination of the user's vitals at one or more time intervals during a sleep session of the user. The at least one health metric can be generated using one or more rules for correlating different types of model outputs to determine the health metric. The at least one health metric can be generated using a model having been trained to correlate different types of model outputs to determine the health metric.

The group of service-providing servers can include a snore detection service-providing server, the snore detection service-providing server being part of the second subset of the group of service-providing servers run at the edge computing device. The snore detection service-providing server can: receive, from an acoustic sensor of the bed system, acoustic signals while the user rests on the bed system, pass the acoustic signals to a snore detection model that is executed at the snore detection service-providing server and configured to generate output indicating whether the user snores while the user rests on the bed system, and transmit the snore detection model output to the messaging service of the cloud-based computing system for further processing.

The group of service-providing servers can also include a sleep stage service-providing server, the sleep stage service-providing server being part of the first subset of the group of service-providing servers run at the cloud-based computing system. The sleep stage service-providing server can: receive, from a pressure sensor of the bed system, pressure signals while the user rests on the bed system, pass the pressure signals to a sleep stage model that is executed at the sleep stage service-providing server and configured to generate output indicating at least heartrate of the user at predetermined time intervals while the user rests on the bed system, and transmit the sleep stage model output to the messaging service of the cloud-based computing system for further processing. The cloud-based computing system can also: transmit, to the snore detection service-providing server via the messaging service, the snore detection model output and a portion of the sleep stage model output, the portion of the sleep stage model output including the predetermined time intervals, and the snore detection service-providing server can correlate identified snore detections in the snore detection model output with the predetermined time intervals to determine when the user snores while resting on the bed system.

The cloud-based computing system can pass the snore detection model output and the sleep stage model output to the aggregator, and the aggregator can correlate the snore detection model output with the sleep stage model output to determine a health condition of the user. Determining the health condition of the user can include applying an aggregation model to the snore detection model output and the sleep stage model output, the aggregation model having been trained to correlate data and determine health conditions of users based on the correlated data.

The cloud-based computing system can include a model training engine, the model training engine being configured to: receive, as training inputs to models that are executed at the group of service-providing servers, the generated sensor signals, model outputs, the at least one health metric, and historic data about a population of users of bed systems, aggregate the received training inputs, iteratively train, for each of the group of service-providing servers, the model that is executed by the service-providing server with a portion of the aggregated training inputs, the portion of the aggregated training inputs having a relationship with the particular sleeper information determined by the model, and pass the trained model to the model wrapping service for wrapping and deployment to the service-providing server.

As another example, the messaging service can load, based on the retrieved data, the model as a plugin and wrap the plugin model. The at least one sensor can include a pressure sensor and the sensor signals can be pressure signals. The at least one sensor can include an audio sensor and the sensor signals can be audio signals. The at least one sensor can include a temperature sensor and the sensor signals can be temperature signals. The at least one sensor can include an array of temperature signals and the sensor signals can be temperature signals. The at least one sensor can include a load cell and the sensor signals can be load cell signals. The at least one sensor can include a combination of any one or more of the group including: pressure sensors, audio sensors, temperature sensors, and load cells. The edge computing device can be a controller of the bed system. The edge computing device can be a pump of the bed system. The edge computing device can include a controller and a pump of the bed system.

In some implementations, the request to execute the model can include information indicating an environment of the requesting service-providing server, the environment being one of the cloud-based system or the edge computing device. The environment of the requesting service-providing server can be defined based on whether the requesting service-providing server is part of the first subset of the group of service-providing servers run in the cloud-based system or the second subset of the group of service-providing servers run at the edge computing device. The retrieved data for executing the model at the requesting service-providing server can include criteria for adjusting computational settings of the model based on the environment of the requesting service-providing server, and the retrieved model can, based on whether the criteria is satisfied, automatically adjust the computational settings of the model to parameterize the model for deployment in the environment of the requesting service-providing server.

In some implementations, the edge computing device can control the one or more components of the bed system. The edge computing device can process at least a portion of the sensor signals generated by the at least one sensor. Each of the group of service-providing servers may run independently of each other.

One or more embodiments described herein can include a system for generating sleeper information based on user data collected at a bed system, the system including: a group of service-providing servers each having one or more processors and memory, each of the group of service-providing servers executing a model for determining particular sleeper information based at least in part on the sensor signals generated by the at least one sensor, a first subset of the group of service-providing servers running in a cloud-based system under cloud-based-system resource constraints and a second subset of the group of service-providing servers running at an edge computing device under edge-computing-device resource constraints. The system can also include a cloud-based computing system having one or more processors and memory, the cloud-based computing system including: a messaging service to: receive, from one or more sensors of a bed system, sensor signals generated by the one or more sensors, and transmit the received sensor signals to a data store for storage, a model wrapping service to: receive, from a service-providing server amongst the group of service-providing servers via the messaging service, a request to execute a model that has a relationship with the service-providing server, retrieve, from the data store via the messaging service, the model and data for executing the model at the requesting service-providing server, the data including at least some of the sensor signals, wrap the model with the retrieved data, and transmit, via the messaging service, the wrapped model and data to the service-providing server for execution, and an aggregator to: receive, from the service-providing server via the messaging service, model output once the wrapped model is executed by the service-providing server and generate at least one health metric about a user of the bed system based on correlating the model output with at least one of (i) other model outputs or (ii) other data about the user.

The system can optionally include one or more of the abovementioned features. In some implementations, the edge computing device can be part of the bed system.

One or more embodiments described herein can include a system for generating sleeper information based on user data collected at a bed system, the system including: a cloud-based computing system having a model-wrapping service, a cloud intelligence engine, and an ingestion layer. The model-wrapping service can generate and wrap each of a group of models for deployment in different computing environments having different resource constraints, a bed system including at least one sensor can generate sensor signals as a user rests on the bed system during a sleep session, and an edge computing device including an edge intelligence engine and a communication service. The edge computing device can: receive, from the cloud-based computing system, at least one wrapped edge-based model, the edge-based model having been wrapped into a data object by the cloud-based computing system, the data object including (i) the edge-based model and (ii) instructions that when executed cause the edge computing device to automatically adjust execution parameters for the edge-based model based on resource constraints of the edge computing device, receive, from the at least one sensor, the generated sensor signals, unwrap, by the edge intelligence engine, the edge-based model in the data object, determine, by the edge intelligence engine, a first set of sleeper information for the sleep session of the user of the bed system based on applying the unwrapped edge-based model to the received sensor signals, and transmit, via the communication service, at least one of the sensor signals and the first set of sleeper information to the cloud-based computing system. The cloud-based computing system can: receive, from the at least one sensor, the generated sensor signals, ingest, from the edge computing device via the ingestion layer, at least one of the sensor signals and the first set of sleeper information, determine, by the cloud intelligence engine, a second set of sleeper information for the user of the bed system based on applying at least one cloud-based model to the received sensor signals and first set of sleeper information, the cloud-based model having been generated by the model-wrapping service to execute according to resource constraints of the cloud-based computing system, the resource constraints of the cloud-based computing system being different than the resource constraints of the edge computing device, and return instructions for presenting the first and second sets of sleeper information to the user of the bed system that, when executed by a computing device of the user, cause the computing device to output at least a portion of the first and second sets of sleeper information for the user in a graphical user interface (GUI) display of the computing device responsive to determining that the sleep session ended.

The system can optionally include one or more of the abovementioned features. The system can optionally include one or more of the following features. For example, the edge computing device can receive, from the at least one sensor, the sensor signals in near real-time as the sensor signals are generated by the at least one sensor during the sleep session. The edge computing device can determine the first set of sleeper information at predetermined time intervals during the sleep session of the user. The predetermined time intervals can be every second during the sleep session. The edge computing device can continuously determine the first set of sleeper information throughout the sleep session of the user. The first set of sleeper information can include intra-sleep information about the user during the sleep session.

The unwrapped edge-based model can determine when the user falls asleep during the sleep session and when the user stays asleep during the sleep session. The unwrapped edge-based model can detect when the user or a partner in the bed system is snoring and automatically adjust a respective side of the bed system based on the snore detection. The unwrapped edge-based model can detect sleep apnea of the user during the sleep session. The unwrapped edge-based model can detect sleep stages of the user during the sleep session. The unwrapped edge-based model can detect bed presence of the user resting on the bed system. The unwrapped edge-based model can determine a heartrate of the user throughout the sleep session. The unwrapped edge-based model can determine a heartrate variability of the user throughout the sleep session. The unwrapped edge-based model can determine a respiratory rate of the user throughout the sleep session. The edge computing device can continuously monitor sleep of the user in near-real time throughout the sleep session.

In some implementations, the cloud-based computing system further includes an aggregator service to determine a sleep metric for the user of the bed system based on applying one or more rules for aggregating the first and second sets of sleeper information. The sleep metric can be a sleep quality score for the sleep session. The sleep metric can be a restful time metric for the sleep session. The sleep metric can be an in/out-of-bed pattern for the sleep session. The sleep metric can be a change in body weight of the user over a threshold quantity of sleep sessions. The sleep metric can be a personalized insight to improve overall sleep quality for the user over a threshold quantity of sleep sessions. The sleep metric can be an apnea risk assessment of the user over a threshold quantity of sleep sessions.

As another example, the second set of sleeper information can include inter-sleep information about the user for at least one of: each sleep session or a threshold quantity of sleep sessions. The cloud-based computing system can receive the generated sensor signals once the sleep session ends and determine the second set of sleeper information after the sleep session. The at least one cloud-based model can determine a skin temperature of the user for the sleep session. The at least one cloud-based model can determine a weight of the user for the sleep session. The at least one cloud-based model can determine an in-bed microclimate for the sleep session. The at least one cloud-based model can determine illness symptoms of the user for the sleep session. The at least one cloud-based model can detect insomnia of the user for the sleep session. The at least one cloud-based model can determine whether the user has an illness or disease over a threshold quantity of sleep sessions.

In some implementations, the edge intelligence engine includes a group of services, each of the plurality of services run independently of each other and execute an edge-based model that has a relationship with the service, where each of the edge-based models can be wrapped, by the model-wrapping service of the cloud-based computing system, in a data object including the edge-based model and instructions that when executed by each of the group of services cause the service to automatically execute the edge-based model under different resource constraints of the service. The cloud-based computing system can transmit, via the communication service to the edge computing device, the data object using mutual authentication techniques.

Sometimes, the received sensor signals and the first set of sleeper information can be temporarily stored in local memory at the edge computing device until transmitted to the cloud-based computing system. Transmitting the at least one of the sensor signals and the first set of sleeper information to the cloud-based computing system can include removing the at least one of the sensor signals and the first set of sleeper information from storage in the local memory. The edge computing device can encrypt the at least one of the sensor signals and the first set of sleeper information before transmission to the cloud-based computing system. The cloud-based computing system can decrypt the at least one of the sensor signals and the first set of sleeper information once ingested, via the ingestion layer. In some implementations, before transmitting the generated sensor signals to the cloud-based computing system, the bed system can anonymize the generated sensor signals and form a client authentication process.

As another example, determining that the sleep session ended can include identifying, by the edge computing device, a sleep-to-wake transition of the user at the bed system. Determining that the sleep session ended can include identifying, by the edge computing device, a bed exit event at the bed system. The cloud-based system can also store, in a data store, the first and second sets of sleeper information in association with the user of the bed system. The cloud-based computing system can also: retrieve, from the data store, at least a portion of the first and second sets of sleeper information, and iteratively train at least one of the edge-based model and the cloud-based model based on the retrieved portion of the first and second sets of sleeper information.

One or more embodiments described herein can include a system for wrapping models for deployment in edge computing environments and cloud-based computing environments of bed systems based on (i) resource constraints of the respective deployment environment and (ii) a type of sleeper information that is determined by the respective wrapped model.

The system can optionally include one or more of the abovementioned features.

One or more embodiments described herein can include a system for determining health information for a user of a bed system, the system including: at least one sensor to generate sensor signals of a user on a bed system, an edge computing device in communication with the at least one sensor, and a remote computing system in communication with the at least one sensor and the edge computing device. The remote computing system can: receive the generated sensor signals from the at least one sensor, receive, from the edge computing device, a request to execute a model to determine a health metric for the user, retrieve, from a data store, data representing the model and instructions for executing the model at the edge computing device, wrap the retrieved data, and transmit the wrapped data to the edge computing device for execution, the wrapped data including instructions that, when executed by the edge computing device, cause the model to automatically adjust to resource constraints of the edge computing device.

The system can optionally include one or more of the abovementioned features. The system can optionally include one or more of the following features. The remote computing system can: retrieve, from the data store, data representing a cloud-based model that was trained to determine a second health metric for the user based on the received sensor signals from the at least one sensor and execute the cloud-based model to determine the second health metric, where executing the cloud-based model can cause the model to automatically adjust to resource constrains of the remote computing system. The remote computing system can: receive model output from the edge computing device upon execution of the model and generate at least one overall health metric for user based on correlating the model output with at least one of (i) other model outputs or (ii) other data about the user. The system can also include a first group of services running at the edge computing device and a second group of services running at the remote computing system. The remote computing system can: receive, from at least one of the first group of services, a request to execute a first model that has a relationship with the at least one of the first group of services, and receive, from at least one of the second group of services, a request to execute a second model that has a relationship with the at least one of the second group of services. The remote computing system can parameterize the first model so that, upon execution by the at least one of the first group of services, the first model automatically adjusts corresponding parameters to execute in an environment of the at least one of the first group of services. The remote computing system can be a cloud-based computing system. The edge computing device can be a controller of the bed system.

One or more embodiments described herein can include a system for determining health information for a user of a bed system, the system including: a remote computing system having one or more processors and memory, the remote computing system being configured to: receive, from one or more sensors of a bed system, sensor signals that are generated by the one or more sensors, receive, from an edge computing device, a request to execute a model to determine a health metric for a user of the bed system, retrieve, from a data store, data representing the model and instructions for executing the model at the edge computing device, wrap the retrieved data, and transmit the wrapped data to the edge computing device for execution, the wrapped data including instructions that, when executed by the edge computing device, cause the model to automatically adjust to resource constraints of the edge computing device.

The system can optionally include one or more of the abovementioned features. Sometimes, the edge computing device can be part of the bed system.

One or more embodiments described herein include a bed system for determining health information for a user of the bed system, the bed system including: at least one sensor to generate sensor signals of a user on the bed system, an edge computing device in communication with the at least one sensor, the edge computing device being configured to: receive, from the at least one sensor, the sensor signals while the user is on the bed system, generate a request to execute a model according to resource constraints of the edge computing device to determine a health metric for the user, transmit the request to a remote computing system having one or more processors and memory, the remote computing system being configured to retrieve, from a data store, data representing the model and instructions for executing the model at the edge computing device according to the resource constraints and wrap the retrieved data, receive the wrapped data from the remote computing system, unwrap the data to automatically adjust parameters of the model for execution according to the resource constraints of the edge computing device, determine, based on applying the model to the received sensor signals, a health metric for the user, and return the health metric for presentation, in a graphical user interface (GUI) display of a computing device, to the user upon a determination that a sleep session of the user ended.

The bed system can optionally include one or more of the abovementioned features.

One or more embodiments described herein can include a system for determining health information about a user at a bed system, the system including: at least one sensor to generate sensor signals of a user on a bed system, an edge computing device to: receive, from the at least one sensor, the generated sensor signals, determine first health information for the user based on applying an edge-based model to the received sensor signals, and transmit the first health information to a remote computing system, and a remote computing system to: receive, from the at least one sensor, the generated sensor signals, receive, from the edge computing device, the first health information, determine second health information for the user based on applying a cloud-based model to the received sensor signals and first health information, and return instructions for presenting at least a portion of the first health information and the second information to the user that, when executed by a computing device of the user, cause the computing device to output the at least portion of the first health information and the second health information in a graphical user interface (GUI) display of the computing device.

The system can optionally include one or more of the abovementioned features.

The devices, system, and techniques described herein may provide one or more of the following advantages. For example, the machine learning models can be configured and deployed in independently-run services in edge and remote computing environments to optimize use of processing power and available compute resources. More specifically, model parameters allow for automatic adjustment of computational requirements of the model so that the model is tuned/able to use all the available resources allocated to a service that executes the model on the edge. After all, each service can operate under different resource constraints on the edge (which may also vary based on a type of user information, health metric, and/or wellness metric that is being determined at the particular service). As a result, the computationally-adjusted model can execute efficiently at the service on the edge (i) without letting the allocated resources at the service go unused during runtime and (ii) without trying to use more than the allocated resources at the service. The disclosed technology also provides for the services to be optimized and orchestrated in a way that allows meeting execution timing constraints. Furthermore, the disclosed technology allows for producing and monitoring metrics for continuously measuring and improving adherence to expected accuracy or its equivalent of the various services that are executed on the edge and and/or remotely. Such metrics can be used to improve model parameterization and model training so that the allocated resources at a particular service of model execution are optimized and efficiently used.

Similarly, operation of one service may not negatively impact operation of another service, especially in the context of using processing power and compute resources that are independently allocated to each service. Since the services are independently-run, if one service crashes or otherwise has an issue, that service's malfunctioning does not affect operation of the other services. The other services can continue to execute and determine user health and/or wellness metrics or other user information while the malfunctioning service(s) is being diagnosed and/or fixed.

Moreover, available processing power and compute resources are efficiently used since a service only executes a model upon receiving a request for a metric that is determined by the service (e.g., a user of a bed system requests to see their heartrate variability during a sleep session at their mobile device). As a result, only that service executes rather than all services, which is a lightweight implementation that advantageously saves on processing power and improves efficiency in determining user information in real-time or near real-time. Because only a requesting service is executed, lighter-weight edge computing resources can also be leveraged to provide accurate and quick information to users where otherwise it would be impossible or more difficult to use these resources to achieve these results.

Cloud computing is flexible and elastic, thereby providing for scalability and additional resources when needed to process data from bed systems and generate robust insights from that data. Cloud computing is also reliable since it provides a centralized system with support in multiple redundant sites. Cloud computing also can be well-maintained and provide centralized, regular maintenance. Moreover, cloud computing reduces costs for adding storage and computational power over time.

Edge computing also provides advantages in the disclosed technology. Edge computing provides for smart data transfers in which valuable data can be intelligently gathered and transmitted to services, other devices, and/or computing systems, rather than mass-gathering all data. Edge computing also improves response time since data processing is performed at the local level in real-time. Moreover, data processing and intelligence determinations at the edge reduce overall costs in processing power and compute resourced for data transmission.

The disclosed technology can also be used to determine and provide deep insights about health and/or wellness metrics and other user information for users of bed systems on timeframes that work for users, instead of making users wait for the processing to happen. As an illustrative example, a user can wake up, grab their phone, and want to see their sleep metrics from last night before getting out of bed. Using the disclosed technology, these sleep metrics can be instantaneously or almost-instantaneously determined and presented at the user's phone. By leveraging deployment of various different machine learning models in different computing environments (edge and remote or cloud-based), the disclosed technology can accurately and quickly identity, detect, and/or determine information about users that otherwise may require massive amounts of data collection, aggregation, and analysis as well as significant amounts of compute resources, processing power, and time. For example, the disclosed technology can be used to identify, detect, and/or determine whether a user develops particular types of illnesses, such as influenza-like symptoms, whether the user develops or has chronic sleep issues and/or health issues, etc. The disclosed technology can also efficiently and accurately generate robust reports about the user's overall health and/or particular health characteristics of concern for the user, such as apnea and snore. The disclosed technology can also generate and provide health alerts to the user, care providers, and other relevant users related to the user in such a way that timely interventions, diagnoses, and/or preventative actions can be made to improve the health of the user.

As another example, the disclosed technology provides for advanced use of artificial intelligence (AI) and/or machine learning (ML) models to run on longitudinal data collected from a variety of sensors of a bed system to accurately identify sleep wellness, chronic sleep issues, and/or chronic health issues of the bed user. The disclosed technology also provides a configurable analytical engine that can be used to define comprehensive techniques for aggregating data and determining different metrics.

The disclosed technology further allows for fast model deployment with low latency, thereby improving overall processing power and ability to achieve computational decisions at various different types of computing systems, including edge computing devices and remote computing systems, such as cloud-based computing systems.

Furthermore, edge computing devices can employ high-performance AI and/or ML algorithms and models to generate longitudinal sleep and/or bio-signal data about users, including intra-sleep metrics (e.g., real-time determinations such as snore and apnea detection). Remote computing systems can provide a scalable infrastructure to further process and store the longitudinal data, including determining inter-sleep metrics (e.g., near real-time or non-real-time determinations such as influence-like illness, skin temperature). The longitudinal aspect of the disclosed technology makes it possible to achieve increased accuracy of models and algorithms that are used to determine valuable insights and metrics about the user that span over multi-night sleep sessions. The remote computing systems can, for example, leverage advanced AI and analytics to generate progressive sleep and/or health insights/metrics about users. Such multistage AI capabilities enable for determination of a comprehensive range of sleep and/or health insights and metrics for users of bed systems. Information determined on the edge and remotely can then be provided through mobile applications launched at user devices to enable direct and ongoing user interaction with advanced performance, health, and sleep monitoring capabilities.

The details of one or more implementations are set forth in the accompanying drawings and the description below. Other features, aspects and potential advantages will be apparent from the accompanying description and figures.

DESCRIPTION OF DRAWINGS

Like reference symbols in the various drawings indicate like elements.

DETAILED DESCRIPTION

The disclosed technology provides bed systems with efficient, lightweight, and accurate end-to-end data processing and insights (e.g., user health metrics, user health information, user sleep metrics) generation. Using the disclosed technology, distributed, independently-run chain-of-data processing services can be run over bed sensor data to obtain raw insights about a user of a bed system. The raw insights can be used as self-invoking triggers for services deployed at an edge computing device, such as a bed controller, to efficiently determine intra-sleep information about the user (e.g., whether the user is snoring, how long it takes the user to fall asleep) and perform reactive actions in real-time or near real-time, such as adjusting a foundation angle of the bed system to stop the user's snoring and/or setting an alarm for the user if the user's partner has a high probability of stroke during the night. The raw insights, as well as the determined intra-sleep information, can also be leveraged as data points for further processing by a remote computing system, such as a cloud-based computing system, to generate inter-sleep information and deeper insights about the user. Such inter-sleep information and deeper insights can include, but are not limited to, identification of chronic sleep and/or health issues, such as influenza. The disclosed technology therefore leverages compute resources and processing power of both edge computing devices and remote computing systems to efficiently generate and provide robust and accurate sleep and health information to users of bed systems.

Figure 1:
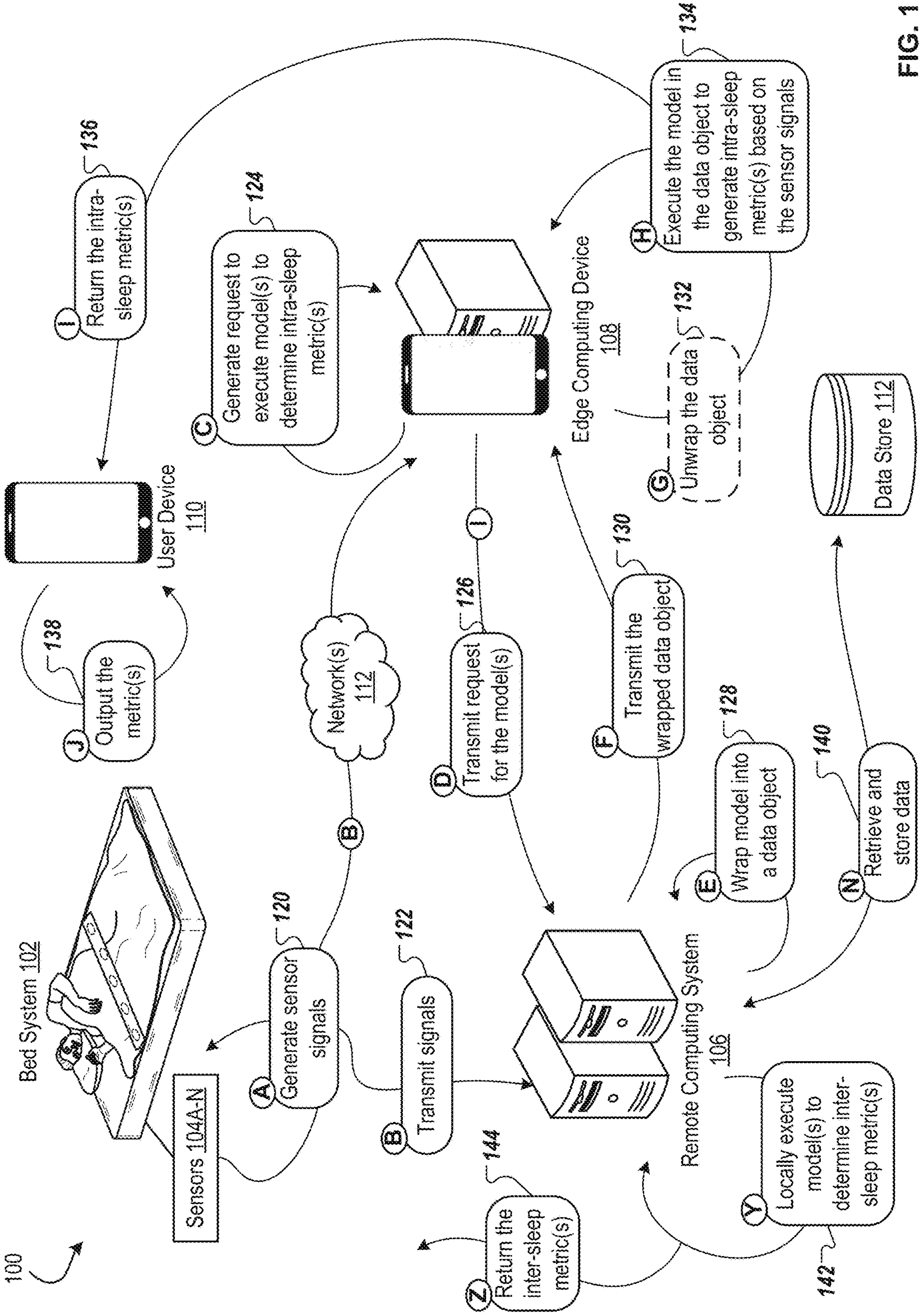
FIG. 1 is a conceptual diagram for generating user information based on data collected at a bed system.

Referring to the figures, FIG. 1 is a conceptual diagram of a system 100 for generating user information based on data collected at a bed system 102. The bed system 102 can communicate over network(s) 112 (e.g., wired and/or wireless communication) with sensors 104A-N, a remote computing system 106, a data store 112, an edge computing device 108, and/or a user device 110.

The bed system 102 can be an air bed system that includes a bed. The bed can include a mattress that includes at least one air chamber surrounded by a resilient border and encapsulated by bed ticking. The resilient border can include any suitable material, such as foam. In some implementations, the resilient border can combine with a top layer or layers of foam to form an upside down foam tub. In other implementations, mattress structure can be varied as suitable for the application. The bed system 102 can also be any other appropriate type of smart bed or adjustable bed system. Sometimes, the bed system 102 can include a mattress having springs. This mattress may not be an air mattress having one or more air chambers. As another example, the bed system 102 can include a mattress and a foundation. The foundation can be adjustable so that the mattress can be automatically positioned at different angles (based on user preference and/or system-made determinations, such as to reduce or otherwise prevent the user from snoring during a sleep session). The bed system 102 can also include a pump, controller, heating/cooling elements/modules (e.g., fans), and/or a remote control. Sometimes, any of these components can be remote from the bed system 102. For example, the user device 110 can include a mobile application that allows the user to control their bed system 102 (e.g., adjust pressure, adjust articulation of the foundation, turn on/off a heating element) from the user device 110 instead of or in addition to the remote control.

The sensors 104A-N can be part of the bed system 102. For example, one or more of the sensors 104A-N can be attached to a top surface of the mattress of the bed system 102. One or more of the sensors 104A-N can be in fluid communication with one or more components of the bed system 102, such as inside an air chamber, in communication with the pump, and/or along a fluid flow path inside the bed system 102. Sometimes, one or more of the sensors 104A-N can be remote from the bed system 102 (e.g., environmental sensors positioned in an environment surrounding the bed system 102, wearable devices having sensors) and in communication with the bed system 102 via the network(s) 112. The sensors 104A-N can include but are not limited to temperature sensors, humidity sensors, pressure sensors, load cells, or other types of sensors having sensing capabilities. The sensors 104A-N can be configured to detect various signals at the bed system 102 when the user rests on the bed system 102.

The remote computing system 106 can be any appropriate type of computing system or network of computing devices that is remote from the bed system 102. The remote computing system 106 can be a cloud-based computing system, for example. The remote computing system 106 can be configured to train machine learning models used for determining information about the user of the bed system 102, wrap the models for deployment in different computing environments, such as at the edge computing device 108, process signals from the sensors 104A-N and/or output from the models deployed at the edge computing device 108, and generate additional information about the user based on the processing.

The edge computing device 108 can be any appropriate type of computing device and/or computing system that is lightweight and configured to operate on edge computing resources and processing power. The edge computing device 108 can, in some implementations, be a controller and/or pump of the bed system 102. As another example, the edge computing device 108 can be the user device 110. The edge computing device 108 can be configured to process the signals from the sensors 104A-N in real-time and/or near real-time and execute the wrapped models at one or more independently-run services to generate intra-sleep information about the user while the user is resting on the bed system 102.

The user device 110 can be any appropriate type of mobile device of the user of the bed system 102, including but not limited to a cellphone, smartphone, tablet, laptop, computer, and/or wearable device. The user device 110 can be used to control components of the bed system 102. The user device 110 can also present a mobile application in a graphical user interface (GUI) display that provides information to the user of the bed system 102, such as information about the bed system 102 and controlling the bed system 102 and/or any of the information (e.g., health information, sleep information, intra-sleep information/metrics, inter-sleep information/metrics) that is determined by the remote computing system 106 and/or the edge computing device 108.

Still referring to the system 100 in FIG. 1, the sensors 104A-N can generate sensor signals in block A (120). The sensors 104A-N can detect phenomena at the bed system 102, such as surface temperature or microclimate of the bed system 102, body temperature of the user, and/or ambient environmental temperature. The sensors 104A-N can additionally or alternatively detect other phenomena, such as humidity, changes in pressure, and/or movement of the user on the bed system 102. The sensor signals can be generated in real-time, as the phenomena is detected. The sensor signals can also be generated in near real-time.

The sensors 104A-N can transmit the signals to the remote computing system 106 and/or the edge computing device 108 over the network(s) 112 (block B, 122). Sometimes, the sensors 104A-N can transmit the signals to the data store 112 for storage and later retrieval by the remote computing system 106 and/or the edge computing device 108. The signals can be transmitted in real-time and/or near real-time (e.g., in batches). Sometimes, the signals may be transmitted, for example to the edge computing device 108), upon a request being made to execute at least one machine learning model to determine metric(s) for the user based on the phenomena detected at the bed system 102 (see blocks C, 124, and Y, 142).

The edge computing device 108 can generate a request to execute at least one model to determine intra-sleep metric(s) for the user of the bed system 102 (block C, 124). As described further in reference to FIGS. 2-4, independently-run services can execute models at the edge computing device 108 as well as the remote computing system 106 in order to determine specific metrics for the user, such as health and/or wellness metrics, sleep metrics, etc. As described herein, the services deployed at the edge computing device 108 can determine intra-sleep metrics for the user while the services deployed at the remote computing system 106 can determine inter-sleep metrics for the user. Each of the services can generate a request for a model that is executed at the service to determine the particular metric or metrics associated with the service. As an illustrative example, an apnea detection service deployed at the edge computing device 108 can request an apnea detection model in block C (124), which can then be executed at the apnea detection service on the edge to determine whether the user experiences apnea during a current sleep session (e.g., a specific intra-sleep metric).

The edge computing device 108 can transmit the request for the model(s) to the remote computing system 106 (block D, 126). The request can be transmitted in real-time or near real-time when it is made by the requesting service (or the edge computing device 108 in general). Sometimes, the request can be transmitted at predetermined times. Sometimes, when multiple services individually request respective models, the requests can be transmitted in batch to the remote computing system 106, even though each service runs independently of the other services.

Figure 9:
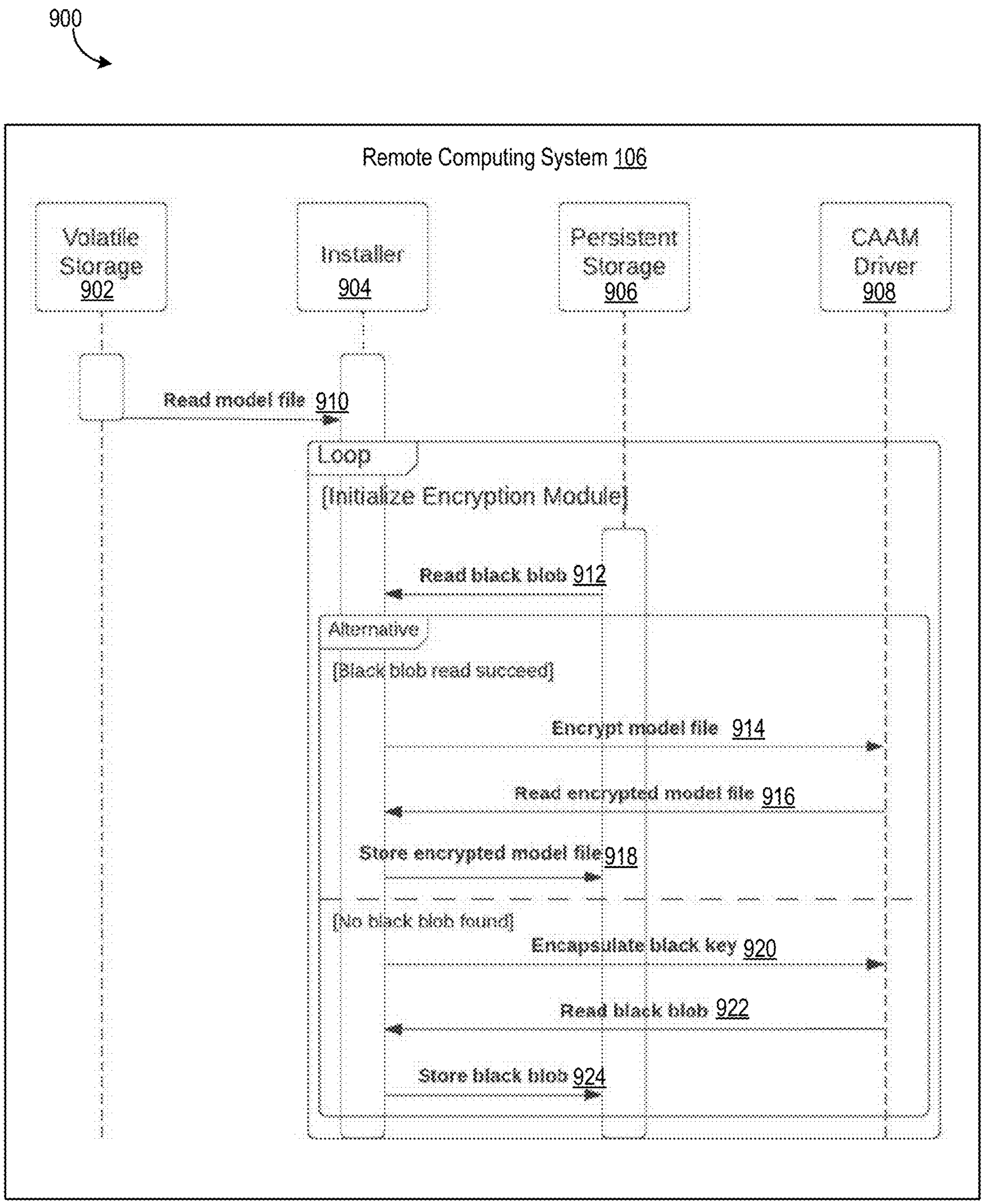
FIG. 9 is a diagram illustrating an example process for encrypting models to transmit to and deploy at an edge computing device.

The remote computing system 106 can wrap the requested model into a data object in block E (128). For example, the remote computing system 106 can retrieve data from the data store 112 (block N, 140) that can be used for wrapping the model and automatically parameterizing the model at the requesting service. Using the retrieved data, the remote computing system 106 can appropriately wrap the model so that it can be executed in accordance with resource constraints at the requesting service at the edge computing device 108. Sometimes, wrapping the model can include encrypting the model, one or more model files, and/or the data object as a whole. Refer to FIG. 9 for further discussion about encrypting the model.

The remote computing system 106 then transmits the wrapped data object to the edge computing device 108 (block F, 130). Once the model is wrapped into the data object, it can be transmitted back to the requesting service at the edge computing device 108. Since services can request their respective model(s) at different times, the wrapped model(s) can be transmitted to the services as they each request the models. Sometimes, the remote computing system 106 can transmit multiple wrapped models back to the edge computing device 108, where each of the multiple wrapped models can be transmitted to the corresponding requesting service.

Figure 10:
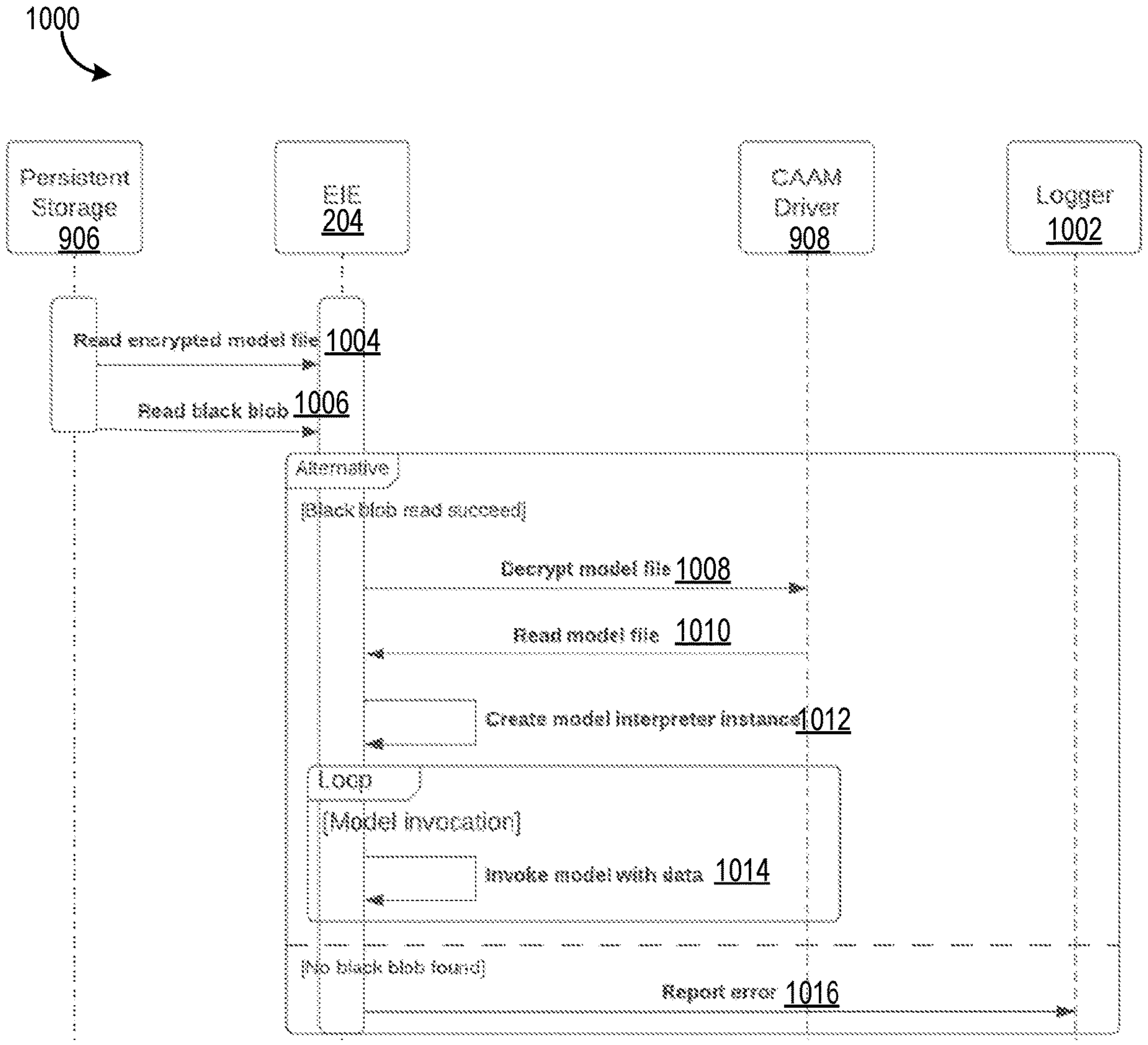
FIG. 10 is a diagram illustrating an example process for decrypting models at an edge computing device for edge-based execution.

Optionally, the edge computing device 108 may unwrap the data object in block G (132). Sometimes, unwrapping the data object can include decrypting the data object and/or one or more model files in the data object. Refer to FIG. 10 for further discussion about the decryption process.

The edge computing device 108, or the requesting service operating at the edge computing device 108, can execute the model in the data object to generate intra-sleep metric(s) for the user based on the received sensor signals (block H, 134). For example, the requesting service can provide the received sensor signals as input to the received model. Output from the model can include the intra-sleep metric that is determined by the requesting service. Sometimes, the requesting service can also provide other inputs to the model, such as one or more data that is included in the data object and/or output from other models executed at other services in the edge computing device 108 and/or the remote computing system 106.

The edge computing device 108 can return the intra-sleep metric(s) to the user device 110 and/or the remote computing system 106 (block I, 136). The intra-sleep metric can, in some implementations, be provided from one service to another service at the edge computing device 108 and/or the remote computing system 106. Thus, the intra-sleep metric can be used as input to one or more other models that are trained to determine other health and/or sleep metrics for the user of the bed system 102.

The user device 110 can output the intra-sleep metric(s) in a GUI display in block J (138). The intra-sleep metric(s) can be outputted in a mobile application that is launched at the user device 110. The intra-sleep metric(s) can be outputted in the mobile application once the user wakes up from the current sleep session and/or launches the mobile application at their user device 110.

The remote computing system 106 can locally execute one or more machine learning models to determine inter-sleep metric(s) for the user (block Y, 142). Block Y (142) can occur during the sleep session of the user and/or after the sleep session or over multiple sleep sessions. Similar to the edge computing device 108, models can be executed by services operating at the remote computing system 106. Each service at the remote computing system 106 can be configured to determine a different inter-sleep metric(s) for the user. Accordingly, the services can run independently from each other, to provide advantages in use of compute resources and processing power, as described herein. Each model executed by each service can receive different data as inputs. The input data can include one or more of the intra-sleep metric(s) that are determined at the edge computing device 108 in block H (134), one or more of the sensor signals received in block B (122), and/or historic user data that the remote computing system 106 retrieves from the data store 112 in block N (140). Therefore, the remote computing system 106 can generate robust health and/or sleep information about the particular user by leveraging available resources and processing power at the remote computing system 106.

Accordingly, the edge computing device's 106 processing power and available compute resources can be used to quickly determine real-time or near real-time information about the user while the processing power and compute resources of the remote computing system 106 can be leveraged to determine more robust insights about the user, such as health conditions and/or sleep conditions that span over an entire sleep session or multiple sleep sessions. The combination of these resources provides for generating accurate information about the user that can benefit the user in the short term as well as in the long term. The information that is quickly and accurately determined at the edge can be used to automatically adjust the user's sleep environment, thereby improving the user's current sleep session and/or health. For example, it can be determined at the edge whether the user is snoring. This determination can be used by the bed system 102 to automatically articulate a foundation of the bed system 102 to elevate the user's head and stop their snoring. The information that is determined remotely (such as in the cloud) can indicate long term and/or chronic conditions of the user, such as whether they are developing an illness. This type of information can be reported to the user or other relevant users, such as caregivers, and used to identify improvements to the user's lifestyle that can help address, prevent, or resolve their chronic condition(s).

Still referring to FIG. 1, the inter-sleep metric(s) that are determined at the remote computing system 106 can be returned in block Z (144) to the user device 110 for output/presentation to the user (block J, 138) and/or the data store 112 for storage (block N, 140). Sometimes, the inter-sleep metric(s) can also be provided as input to one or more of the models described herein to generate more robust insights, health and/or wellness metrics, and/or sleep metrics about the user of the bed system 102.

In some implementations, blocks A-H can be performed during a sleep session of the user. Blocks Y, Z, I, and/or J can be performed after the sleep session of the user (e.g., once a bed-exit event is detected at the bed system 102 based on analyzing a change in pressure signals from the sensors 104A-N), such as immediately after, some threshold amount of time after, and/or upon receiving a request from the user device 110 for health and/or sleep metrics for the user. Sometimes, one or more of the blocks Y, Z, I, and J can also be performed during the sleep session of the user. Any one or more of the blocks A-Z in FIG. 1 can be performed at different times before, during, and/or after a sleep session or multiple sleep sessions of the user.

Figure 2:
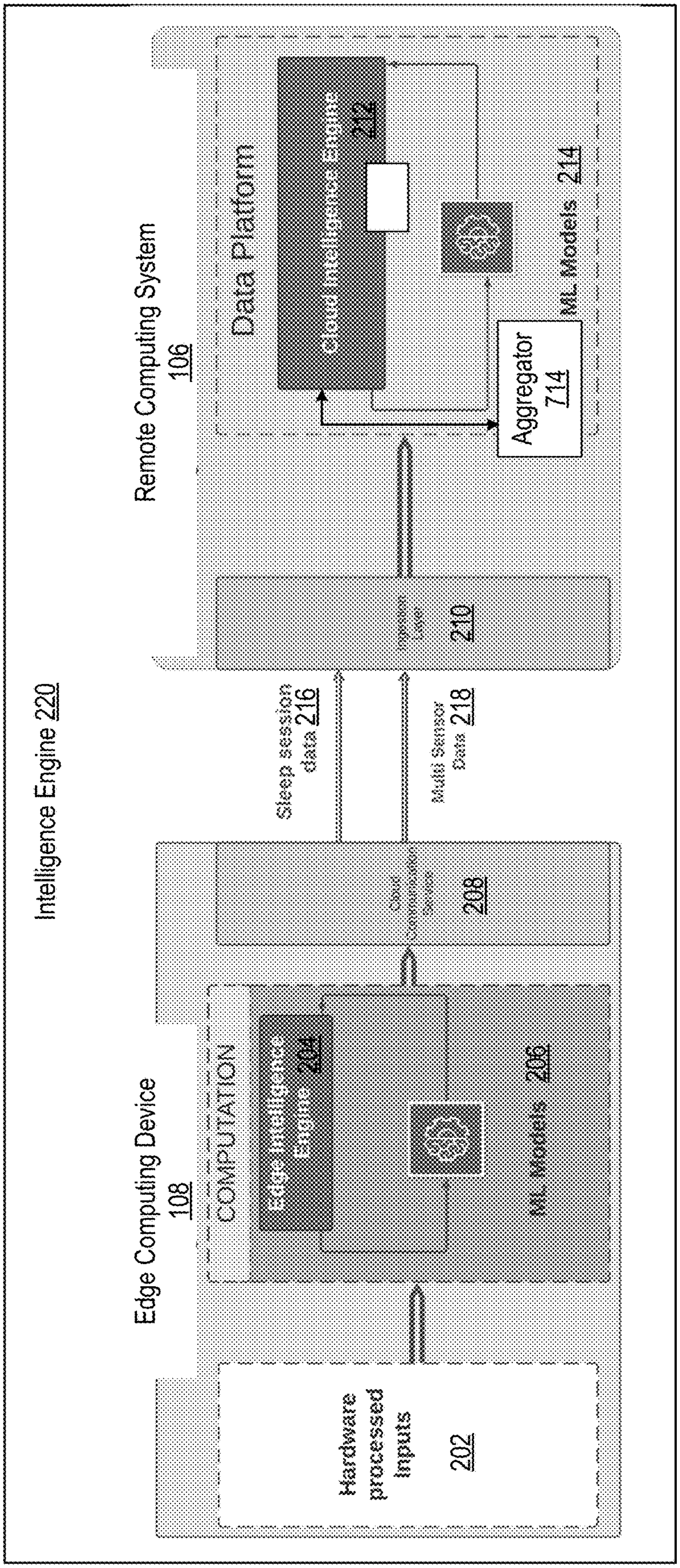
FIG. 2 is a block diagram of an example intelligence engine for performing the techniques described herein.

FIG. 2 is a block diagram of an example intelligence engine 220 for performing the techniques described herein. The intelligence engine 220 can be composed of both the edge computing device 108 and the remote computing system 106. The edge computing device 108 can include an edge intelligence engine 204. The remote computing system 106 can include a cloud intelligence engine 212 having a machine learning execution environment. Both engines 204 and 212 can serve to deliver real-time or near real-time insights/metrics about a user's sleep quality and/or health. As described herein, the edge intelligence engine 204 of the edge computing device 108 can operate at a bed system-level to deliver insights/metrics about the user's sleep patterns during a particular sleep session. Operations of the intelligence engine 220 can create longitudinal data to be used separately or in aggregation for the generation of robust health and sleep insights/metrics about the user. As a result, real-time and accurate insights about the user's current sleep session and multiple sleep sessions over time can be delivered to the user.

Both the edge intelligence engine 204 and the cloud intelligence engine 212 can work in unison to facilitate strategic capabilities in providing users with sleep insights/metrics. This can be achieved by aggregating different data types, by providing a historical data view, and by determined intra-sleep session metrics and inter-sleep session metrics for the user. In other words, the edge intelligence engine 204 can work with the cloud intelligence engine 212 (e.g., collaborate) to generate insights and metrics for the users. The edge intelligence engine 204, for example, can generate insights, metrics, or other data that can also be provided to the cloud intelligence engine 212 as input to generate aggregated, more complex, or other types of insights and metrics for the users. The edge intelligence engine 204 can therefore generate different types of data that can be leveraged by the cloud intelligence engine 212 to generate more insights and metrics for the users.

The edge intelligence engine 204 can receive hardware processed inputs (202). These inputs can be sensor signals generated by sensors at a bed system, as described in reference to FIG. 1. The sensor signals can be provided as inputs to one or more ML models 206 that are executed by the edge intelligence engine 204. As described herein, the edge intelligence engine 204 can run multiple, independent services. Each service can execute a different model 206 to determine a different sleep and/or health insight/metric for a user. The edge intelligence engine 204 can receive raw sensor data as the inputs 202 to be used in real-time insight generation and inferences made by the models 206 executing on the edge.

The edge intelligence engine 204 can also communication with the remote computing system 106 via a communication service 208. The edge intelligence engine 204 can transmit sleep session data 216 (e.g., sleep and/or health insights that are determined by executing one or more of the models 206 at the edge intelligence engine 204) and/or multi-sensor data 218 (e.g., raw sensor signals that are generated by the hardware of the bed system) to the remote computing system 106 via the service 208. For example, the edge computing device 108 can receive the raw sensor signals as the inputs 202 from the hardware (e.g., sensors) of the bed system, then transmit the raw sensor signals as data 216 and/or 218 to the remote computing system 106 for storage and/or further processing.

The remote computing system 106 can include a messaging service 210 (e.g., ingestion layer), which can be configured to receive or ingest the sleep session data 216 and/or the multi-sensor data 218 from the edge computing device 108. The messaging service 210 and/or the communication service 208 can be standard messaging queues through which all services that execute at the edge computing device 108 and the remote computing system 106 communicate/interact.

The data 216 and/or 218 that are ingested into the remote computing system 106 by the messaging service 210 can then be fed to the cloud intelligence engine 212 and/or an aggregator 714. The cloud intelligence engine 212 can be configured to execute one or more machine learning models 214 to generate additional insights/metrics about the user's sleep and/or health. As described herein, the engine 212 can run several services, where each service is independently run and executes a particular model to determine a particular insight/metric for the user. One or more of the models 214 can receive both sleep session data 216 and multi-sensor data 218 as inputs. One or more of the models 214 may receive only the sleep session data 216 or the multi-sensor data 218 as inputs. In some implementations, one or more of the models 214 may additionally or alternatively receive historic user data to generate insights/metrics for the user.

The cloud intelligence engine 212 can also be configured to train and/or continuously improve any of the models 206 and 214 with the data 216 and/or 218. The models 206 and 214 can be trained, evaluated, and stored at/by the remote computing system 106. Moreover, for the models 206 to execute at the edge computing device 108, the edge computing device 108 requests the models from the remote computing system 106. The remote computing system 106 can therefore serve any of the requested models 206 via the messaging service 210. As described further throughout this disclosure (e.g., refer to FIGS. 9-10), the cloud intelligence engine 212 can wrap the requested models in data objects and encrypt the data objects for safe transfer to the edge computing device 108. The edge computing device 108 can then unwrap the data object and/or decrypt the data object in order to execute the requested models 206 by the services in the edge intelligence engine 204. The remote computing system 106 can also execute one or more of the models 214 for generating insights/metrics about the user in near real-time.

The aggregator 714, for example, can be configured to take output from the models 206 executed at the services in the edge intelligence engine 204 and/or output from the models 214 executed at the services in the cloud intelligence engine 212 and correlate that output to make inferences about the user's health and/or sleep. The aggregator 714 can determine the user's vitals at various times during a current sleep session and/or over multiple sleep sessions. The aggregator 714 can also infer chronic health and/or sleep conditions of the user based on correlating various information about the user that was determined on the edge or remotely in the cloud.

Figure 3A:
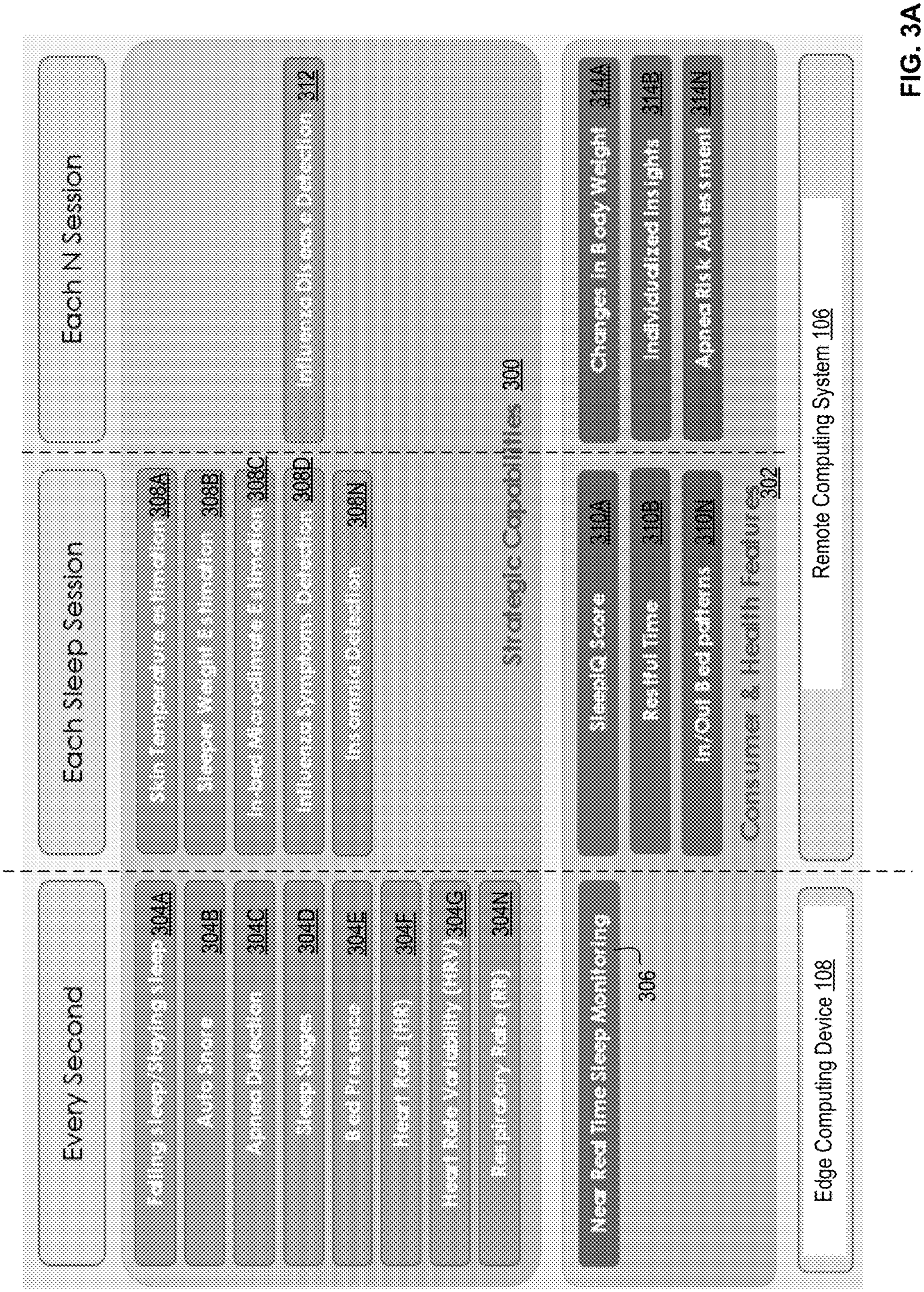
FIG. 3A is a block diagram of example intra-sleep determinations made with edge-based computing and inter-sleep determinations made with remote-based computing.

FIG. 3A is a block diagram of example intra-sleep determinations 304A-N and 306 made with edge-based computing and inter-sleep determinations 308A-N, 310A-N, 312, and 314A-N made with remote-based computing. As described herein, the disclosed technology provides a wide range of sleep, health, and/or wellness metrics that can be determined by the edge computing device 108 and the remote computing system 106. The collection and processing of longitudinal data over multiple-night sleep sessions also makes it possible to achieve increased accuracy for models to determine sleep and health metrics for users of bed systems.

Every second or other predetermined time intervals during a sleep session (e.g., every 0.5 seconds, every 3 seconds, every 5 seconds, every 10 seconds, every 15 seconds, every minute), the edge computing device 108 has various strategic capabilities 300 that include determining one or more intra-sleep metrics 304A-N. Each of the intra-sleep metrics 304A-N can be determined at an independently-run service operating at the edge computing device 108 and using available edge computing resources. As described herein, since the services are independently-run, each service may execute a model to determine a respective intra-sleep metric 304A-N without having to wait for or execute other models at other services to determine other intra-sleep metrics 304A-N. As a result, edge computing resources can be efficiently used to accurately and quickly determine any one or more of the intra-sleep metrics 304A-N every second during the user's sleep session.

Figure 4A:
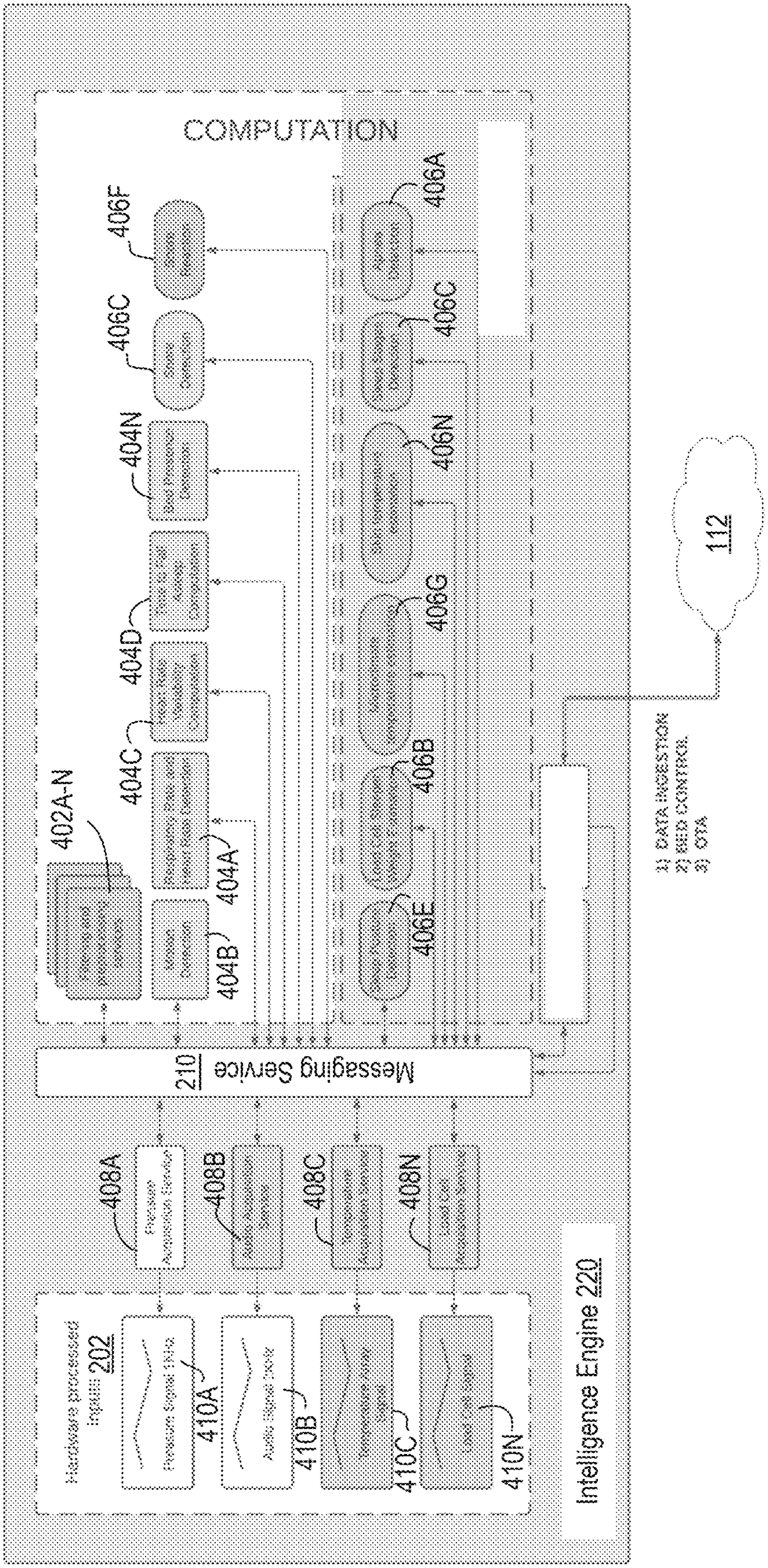
FIG. 4A is a block diagram of an example intelligence engine for generating user information based on data collected at a bed system.
Figure 4B:
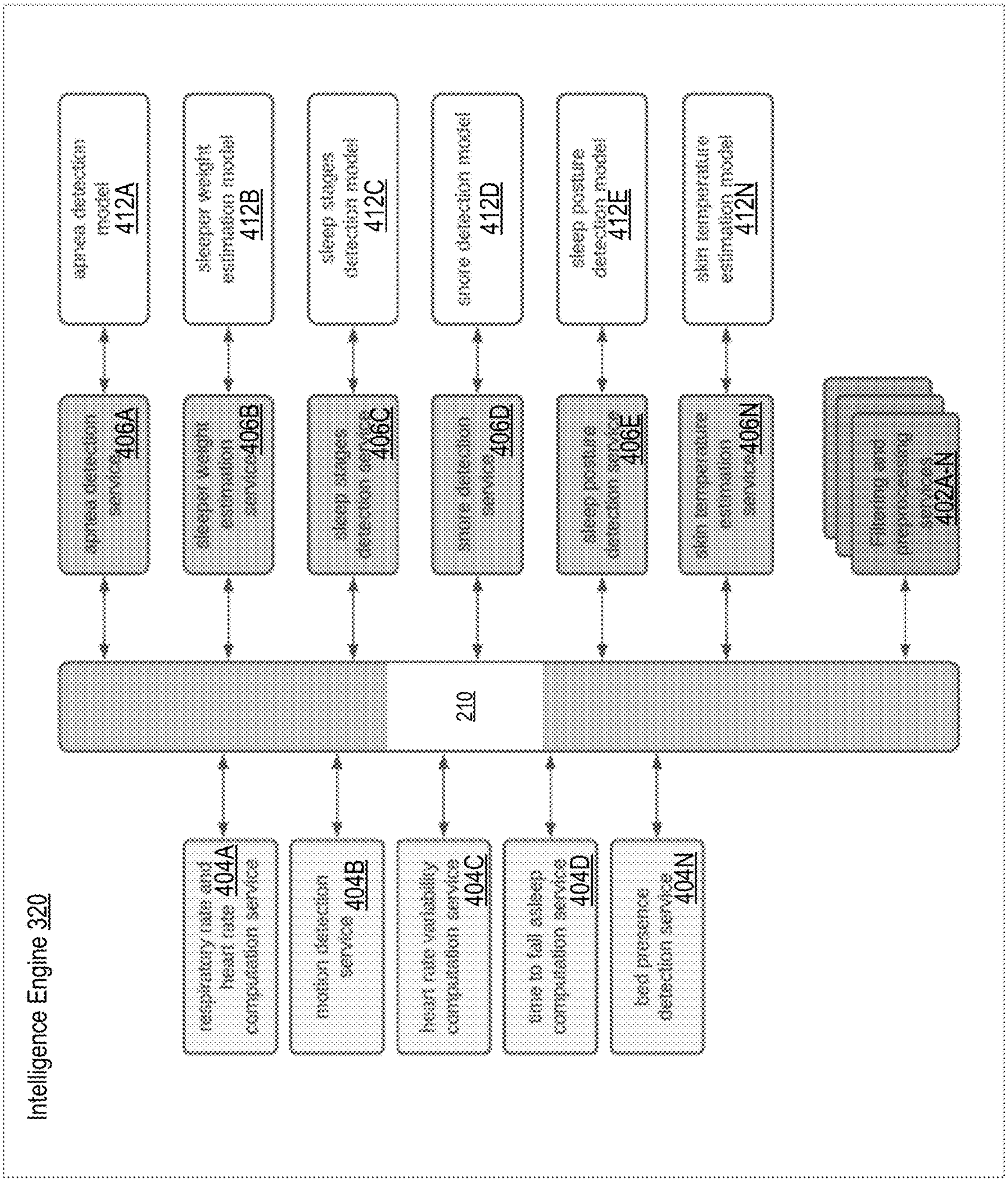
FIG. 4B is a block diagram of example services that can be executed in the intelligence engine of FIG. 4A to generate the user information.
Figure 4C:
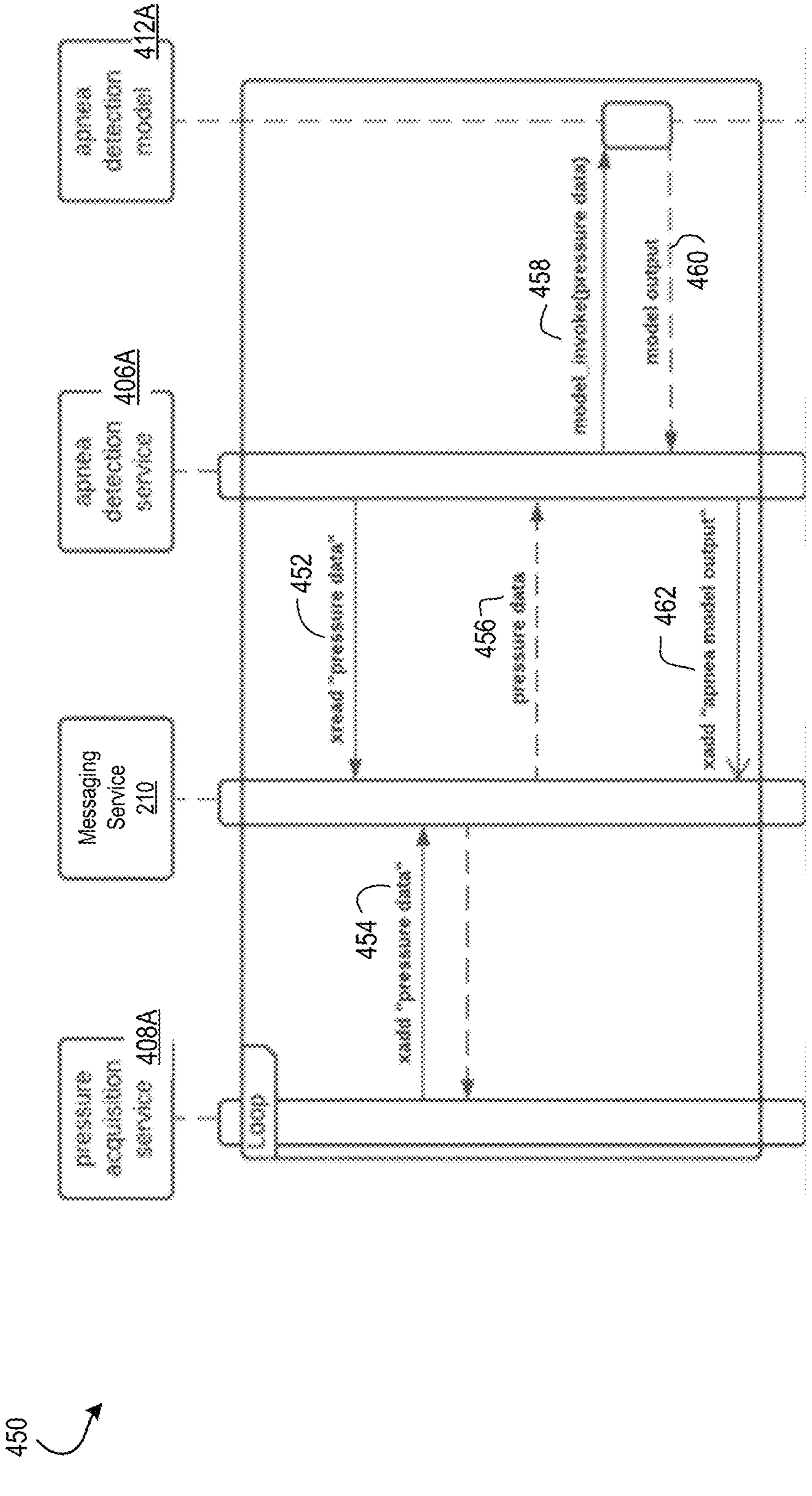
FIG. 4C is a diagram of an example process for invoking and executing a model at an apnea detection service described in FIG. 4B.

The intra-sleep metrics 304A-N can include but are not limited to: a falling asleep/staying asleep metric 304A, auto snore metric 304B, apnea detection metric 304C, sleep stages metric 304D, bed presence metric 304E, heartrate (HR) metric 304F, heartrate variability (HRV) metric 304G, and a respiratory rate (RR) metric 304N. One or more additional or fewer intra-sleep metrics 304A-N may be determined at the edge computing device 108. Refer to FIGS. 4A-C for further discussion about determining the metrics 304A-N.

The edge computing device 108 can also provide user and health features 302 every second or other predetermined time interval during the sleep session. For example, the edge computing device 108 can provide near real-time sleep monitoring 306 for the user. The edge computing device 108 can receive sensor signals from sensors of the bed system and process the sensor signals to determine sleep monitoring metrics for the user. The sleep monitoring 306 can include any one or combination of the intra-sleep metrics 304A-N that are determined as part of the strategic capabilities 300 of the edge computing device 108. The near real-time sleep monitoring 306 can be provided to, outputted/presented at a user device of the user. The near real-time sleep monitoring 306 can also be transmitted to devices of relevant users, such as care providers for the user, who can monitor the conditions of the user while they are asleep (e.g., monitoring whether the user's HR drops below a healthy level for the user's particular health condition(s)).

The remote computing system 106 can provide strategic capabilities 300 and user and health features 302 during both each sleep session of the user and over multiple (e.g., N) sleep sessions of the user. Each sleep session, for example, services independently running at the remote computing system 106 can determine one or more of the following: skin temperature estimation 308A, sleeper weight estimation 308B, in-bed microclimate estimation 308C, influenza or other illness symptoms detection 308D, and insomnia detection 308N. One or more additional or other inter-sleep metrics 308A-N can also be determined by the remote computing system 106 during the sleep session of the user. Any one or more of the inter-sleep metrics 308A-N can also be determined by using the intra-sleep metrics 304A-N, historic user data, and/or sensor signals as inputs to models that are executed at the services.

During each sleep session, the remote computing system 106 can also provide one or more of the following user and health features 302, which can be presented at the user device of the user as described herein: a sleep quality score 310A, a restful time metric 310B, and/or in and out of bed patterns 310N.

Over a predetermined quantity of sleep sessions, the remote computing system 106 can determine influenza or other illness disease detection 312. This determination can be made using one or more of the inter-sleep metrics 308A-N, intra-sleep metrics 304A-N, historic user data, and/or sensor signals as inputs to a model that is trained to determine whether the user has or is developing some illness or disease, such as influenza. The remote computing system 106 can also determine one or more other inter-sleep metrics over the predetermined quantity of sleep sessions.

Over the predetermined quantity of sleep sessions, the remote computing system 106 can also provide user and health features 302 to be presented to the user at their respective device that include, but are not limited to: changes in body weight over the predetermined quantity of sleep sessions 314A, individualized insights 314B to help the user improve their sleep, health, and/or habits, and/or apnea risk assessment 314N. One or more other user and health features 302 can be determined and presented by the remote computing system 106 to the user over the predetermined quantity of sleep sessions.

Figure 3B:
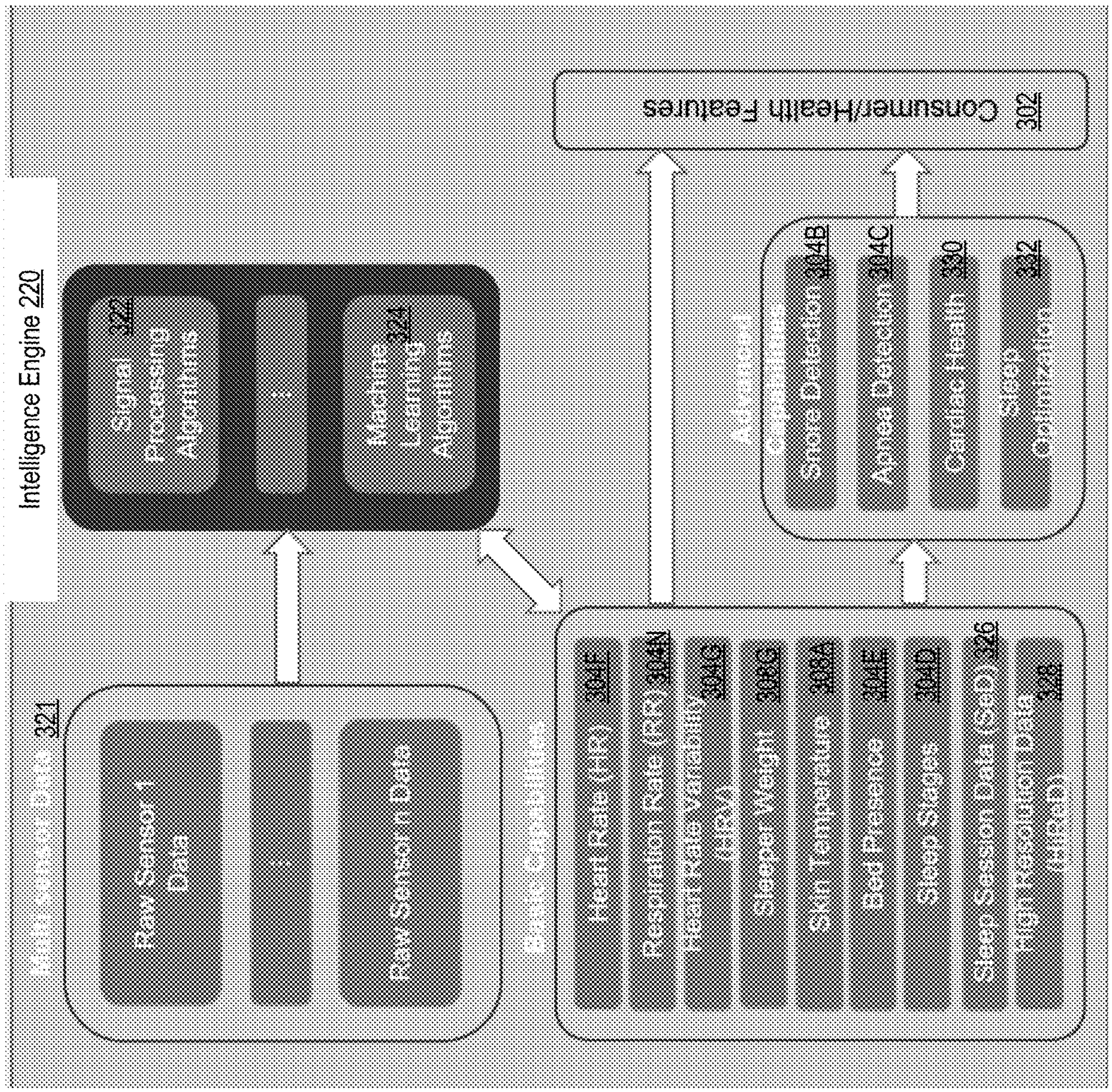
FIG. 3B is a block diagram of example edge-based and remote-based computing that is performed to deliver health metrics and information to a user.

FIG. 3B is a block diagram of example edge-based and remote-based computing that is performed to deliver health and/or wellness metrics and information to a user. More particularly, FIG. 3B shows an example use case for running a distributed chain of data processing services over bed sensors data to obtain raw insights about the user during a sleep session.

The intelligence engine 220, which includes the edge computing device 108 and the remote computing system 106 as described in reference to FIG. 2, can receive multi-sensor data 321. The multi-sensor data 321 can include raw sensor data 1-*n*, which can be generated by any sensors at the user's bed system and/or worn by the user (e.g., a wearable device, such as a smart watch). The raw insights can be used by services operating on the edge to generate and execute reactive behaviors during the sleep session, such as adjusting a foundation of the user's bed to stop the user's snoring. The raw insights can also be used by services operating in the cloud or remotely from the edge or the bed to determine deeper, more robust health and/or sleep insights/metrics about the user. As illustrative examples, machine learning models can be used to process edge-streamed data and to detect symptoms of various conditions, including but not limited to influenza and other health concerns. Signal processing algorithms can also be applied to edge-streamed data in order to monitor biometric information about the user and present the biometric information to the user at the user's mobile computing device.

For example, one or more services operating on the edge or remotely in the intelligence engine 220 can implement one or more signal processing algorithms 322 and machine learning models/algorithms 324 to determine metrics 304A-N, 308A-N, 326, and/or 328 (refer to FIG. 3A for further discussion about some of the metrics 308A-N and 308A-N). For example, the algorithms and/or models 322 and 324 can be used to determine HR (304F), RR (304N), HRV (304G), sleeper weight (308G), skin temperature (308A), bed presence (304E), sleep stages (304D), sleep session data, SeD (326), and/or high resolution user data, HiReD (328).

Any of the metrics 304A-N, 308A-N, 326, and/or 328 can further be used as inputs to one or more models on the edge or in the cloud to determine additional metrics 304A-N, 330, and/or 332 about the user. For example, the algorithms and/or models 322 and 324 can further be used to determine snore detection (304B), apnea detection (304C), cardiac health (330), and/or sleep optimization (332).

Any of the metrics 304A-N, 308A-N, 326, 328, 330, and/or 332 can also be delivered to the user at their computing device as user and health features 302.

FIG. 4A is a block diagram of the intelligence engine 220 for generating user information based on data collected at a bed system. As described throughout this disclosure, hardware processed inputs 202 can be ingested into the intelligence engine 220 by the messaging service 210. The inputs 202 can be generated by sensors at the bed system. For example, the inputs 202 can include pressure signals 410A, audio signals 410B, temperature array signals 410C, and/or load cell signals 410N. One or more other signals may also be processed as the inputs 202.

Services 408A-N can operate at the bed system (e.g., on the edge at the edge computing device 108) to process and provide the signals 410A-N via the messaging service 210 to one or more other services in the intelligence engine 220. The other services in the intelligence engine 220 can operate on the edge or remotely in the cloud and can apply machine learning models to determine intra-sleep and inter-sleep metrics about the user.

The services 408A-N can include but are not limited to a pressure acquisition service 408A, an audio acquisition service 408B, a temperature acquisition service 408C, and a load cell acquisition service 408N. The pressure acquisition service 408A can be configured to receive the raw pressure signals 410A from pressure sensors of the bed system or around/near the bed system. The service 408A can process/filter the signals 410A and transmit the signals 410A via the messaging service 210 to one or more services operating in the intelligence engine 220 to be provided as input to one or more models.

The audio acquisition service 408B can be configured to receive the raw audio signals 410B from audio sensors of the bed system or around/near the bed system. The service 408B can process/filter the signals 410B and transmit the signals 410B via the messaging service 210 to one or more services operating in the intelligence engine 220 to be provided as input to the one or more models.

The temperature acquisition service 408C can be configured to receive the raw temperature array signals 410C from temperature sensors of the bed system or around/near the bed system. The service 408C can process/filter the signals 410C and transmit the signals 410C via the messaging service 210 to one or more services operating in the intelligence engine 220 to be provided as input to the one or more models.

The load cell acquisition service 408N can be configured to receive the raw load cell signals 410N from load cells of the bed system or around/near the bed system. The service 408N can process/filter the signals 410N and transmit the signals 410N via the messaging service 210 to one or more services operating in the intelligence engine 220 to be provided as input to the one or more models.

In the intelligence engine 220, any one or more of the signals 410A-N can be filtered and/or pre-processed by filtering and pre-processing services 402A-N. The services 402A-N can operate on the edge, for example at the edge computing device 108. Each service 402A-N can be configured to filter and/or pre-process a different type of sensor signal received via the messaging service 210 from the acquisition services 408A-N. Sometimes, the acquisition services 408A-N can simply receive the signals 410A-N from the sensors of the bed system and transmit the signals 410A-N directly to the filtering and pre-processing services 402A-N. The filtered and pre-processed signals can then be transmitted to one or more services 404A-N and/or 406A-N operating in the intelligence engine 220. Sometimes, the raw signals 410A-N from the acquisition services 408A-N can be directly transmitted to the services 404A-N and 406A-N.

The services 404A-N and 406A-N can run independent of each other. Some of the services 404A-N and 406A-N can operate on the edge at the edge computing device 108 while other services 404A-N and 406A-N can operate remotely, such as in the cloud, at the remote computing system 106.

The services 404A-N can include but are not limited to: a RR and HR detection service 404A, a motion detection service 404B, an HRV computation service 404C, a time-to-fall asleep computation service 404D, and a bed presence detection service 404N. The RR and HR detection service 404A can run on the edge at the edge computing device 108. Every second or other predetermined time interval, the service 404A can use one or more of the signals 410A-N (e.g., pressure signals collected on a top surface of the bed system) as input to an HR detection model and/or an RR detection model to determine the user's real-time or near real-time HR and/or RR. The motion detection service 404B, which runs on the edge, can, every second or other predetermined time interval, determine whether, when, and how much the user moves in bed using one or more of the signals 410A-N (e.g., pressure signals, load cell signals, temperature signals) as input to a motion detection machine learning model. Every second or other predetermined time interval, the HRV computation service 404C, which runs on the edge, can use one or more of the signals 410A-N (e.g., pressure signals collected on the top surface of the bed system) as input to an HRV detection model to determine the user's real-time or near real-time HRV. Every second or other predetermined time interval, the time-to-fall asleep service 404D, which runs on the edge, can use one or more of the signals 410A-N (e.g., pressure signals) as input to a machine learning model to determine when the user falls asleep, how long they stay asleep, and/or when they wake up. Every second or other predetermined time interval, the bed presence detection service 404N, which runs on the edge, can use one or more of the signals 410A-N (e.g., pressure signals, load cell signals, temperature signals collected on the top surface of the bed system, audio signals) as input to bed presence detection model to when the user is in bed and/or when the user exits the bed.

The services 406A-N can include but are not limited to: an apnea detection service 406A, a load cell sleeper weight estimation service 406B, a sleep stages detection service 406C, sleep posture detection service 406E, a snore reaction service 406F, microclimate temperature estimation service 406G, and skin temperature estimation service 406N. Every second or other predetermined time interval, the apnea detection service 406A, which runs on the edge, can use one or more of the signals 410A-N (e.g., pressure signals, audio signals) as input to an apnea detection model to determine whether the user experiences apnea during their sleep session. During each sleep session and/or after a sleep session, the load cell sleeper weight estimation service 406B, which runs remotely at the remote computing system 106, can use one or more of the signals 410A-N (e.g., pressure signals, load cell signals) as input to an weight estimation model to determine the user's current weight and/or changes in the user's weight over time (e.g., over a threshold amount of sleep sessions). Every second or other predetermined time interval, the sleep stages detection service 406C, which runs on the edge, can use one or more of the signals 410A-N (e.g., pressure signals, temperature signals, load cell signals) as input to a sleep stage detection model to identify what sleep stage the user is currently in, going into, and/or otherwise determine the user's sleep stages during a sleep session.

Every second or other predetermined time interval, the sleep posture detection service 406E, which runs on the edge, can use one or more of the signals 410A-N (e.g., pressure signals, temperature) as input to a posture detection model and to determine the user's real-time or near real-time changes in posture throughout the sleep session. Every second or other predetermined time interval, the snore reaction service 406F, which runs on the edge, can use one or more of the signals 410A-N (e.g., pressure signals, audio signals) as input to a snore detection model and to determine when the user snores and what automated adjustments can be made to the bed system to respond to/stop the snoring (e.g., incline a head end of a bed foundation to a predetermined angle). Determinations made by the service 406F can be transmitted to one or more bed controller components to automatically adjust the bed system in real-time.

During the sleep session and/or a threshold amount of time after the sleep session, the microclimate temperature estimation service 406G, which can run remotely at the remote computing system 106, can use one or more of the signals 410A-N (e.g., temperature signals) as input to a microclimate determination model to determine temperatures at a top surface of the bed system throughout the user's sleep session. During the sleep session and/or a threshold amount of time after the sleep session, the skin temperature estimation service 406N, which can run remotely at the remote computing system 106, can use one or more of the signals 410A-N (e.g., temperature signals, pressure signals) as input to a skin temperature determination model to monitor and determine temperatures of the user's body throughout the user's sleep session.

Any of the determinations made by the services 404A-N and 406A-N can then be transmitted via the network(s) 112 to one or more devices and systems. For example, one or more of the determinations can be transmitted to a user device of the user of the bed system for display in a mobile application. One or more of the determinations can also be transmitted to a bed controller, pump, or other control system of the bed system to automatically control one or more components of the bed system. The determinations can also be transmitted to a data store for storage and retrieval at a later time for additional processing (e.g., additional processing by the remote computing system 106 to determine multi-night sleep session insights/metrics about the user).

One or more of the determinations can also be provided as input to one or more other services and/or models (e.g., the aggregator 714) to determine deeper insights and metrics about the user's health and/or sleep. For example, a combination of HR, skin temperature, sleep stages, and RR determinations can be processed with a model to determine that the user is developing influenza-like symptoms or some other illness. This determination can be made by a service that runs remotely in the cloud at the remote computing system 106 during the current sleep session, a threshold amount of time after the sleep session, and/or over a threshold quantity of sleep sessions. Refer to FIG. 3A for further discussion about aggregating various service determinations to generate deeper insights/metrics about the user.

FIG. 4B is a block diagram of example services 402A-N, 404A-N, and 406A-N that can be executed in the intelligence engine of FIG. 4A to generate the user information (e.g., sleep and health insights and metrics). As described herein, the services 402A-N, 404A-N, and 406A-N can be independently run and can communicate with each other, components of the bed system (e.g., sensors), and/or other computing systems/devices via the messaging service 210. Since the services 402A-N, 404A-N, and 406A-N are independently-run, each service implements its own data acquisition logic.

Although the services 402A-N, 404A-N, and 406A-N are independently-run, they all have a common requirement to deliver data in a timely manner (e.g., in real-time or near real-time during a sleep session of the user, a threshold amount of time after the sleep session, after a threshold quantity of sleep sessions). A service that must return data in real-time or near real-time (to be used in another determination, for example), can be assigned higher priority than another service for execution and/or use of available compute resources and processing power in the service's execution environment. For example, one or more of the services 404A-N can be given higher priority than the services 406A-N. The services 406A-N may not execute until it is determined whether the user is actually in bed (which can be determined by the motion detection service 404B or the bed presence detection service 404N).

Some of the services, such as the services 402A-N, 404A-N, 406A, and 406C-E can operate on the edge at the edge computing device 108. These services can execute during a sleep session of the user to determine real-time or near real-time metrics about the user. Other services, including but not limited to the services 406B and 406N can operate in the cloud (e.g., remotely) at the remote computing system 106. These services can operate after the sleep session, at predetermined times throughout the sleep session of the user, and/or after a threshold quantity of sleep sessions.

As shown in FIG. 4C, each of the services 406A-N can execute respective models 408A-N to make one or more determinations. The models 412A-N executing on the edge can be wrapped at the remote computing system 106, then transmitted to the edge for execution in their respective services 406A-N. Although not shown in FIG. 4B, one or more models may also be executed at the services operating remotely at the remote computing system 106. However, the models executed at the remote computing system 106 may not be wrapped since they are not being transmitted across networks for execution in another computing environment. Furthermore, although not shown in FIG. 4B, the services 404A-N may also execute respective models to make determinations on the edge.

The apnea detection service 406A can execute an apnea detection model 412A to determine whether the user has apnea during a sleep session. The model 412A can be transmitted to the service 406A from the remote computing system 106 via the messaging service 210. For example, as described herein, when the apnea detection service 406A executes (e.g., because the user selected an option in a mobile application presented at their device to monitor their sleeping patterns for apnea, because the service automatically executes during every sleep session to check the user for apnea), the service 406A sends a request for the model 412A to the remote computing system 106. The remote computing system 106 then retrieves the model 412A from a data store or other storage, wraps the model 412A with data and instructions for execution in the computing environment of the service 406A, and transmits the wrapped model 412A back to the service 406A. The service 406A may then use one or more of the sensor signals that are generated by sensors at the bed system and filtered and/or pre-processed by the services 402A-N as inputs to the model 412A to determine whether the user has apnea. The service 406A may also use one or more outputs/determinations from the other services 404A-N and 406A-N as inputs to the model 412A. Refer to FIG. 4C for further description about executing the model 412A at the service 406A. Output from the model 412A can be transmitted via the messaging service 210 back to the remote computing system 106, to one or more other services 404A-B and/or 406A-B, to the data store for storage, and/or to the user's computing device for presentation to the user.

The sleeper weight estimation service 406B can execute a sleeper weight estimation model 412B to determine a current weight of the user for the sleep session and/or a change in weight of the user over the sleep session or over a threshold quantity of sleep sessions. The service 406B can request and execute the model 412B similarly as described above in reference to the apnea detection service 406A.

The sleep stages detection service 406C can execute a sleep stages detection model 412C to detect/determine the user's sleep stages, how long the user remains in each sleep stage, and/or which sleep stage the user is currently in during the sleep session. The service 406C can request and execute the model 412C similarly as described above in reference to the apnea detection service 406A.

The snore detection service 406D can execute a snore detection model 412D to determine whether and when the user snores during the sleep session. Sometimes, the model 412D can also determine one or more responsive actions/behaviors that can be performed at the bed system of the user to stop the user's snoring (e.g., adjusting a foundation of the bed system by a threshold amount). Sometimes, the model 412D can be used to determine whether and when the user's bed partner snores during the sleep session and optionally one or more responsive actions to prevent or stop the partner's snore. The service 406D can request and execute the model 412D similarly as described above in reference to the apnea detection service 406A.

The sleep posture service 406E can execute a sleep posture detection model 412E to determine movements of the user and/or positions that the user rests in while on the bed system during the sleep session. The service 406E can request and execute the model 412E similarly as described above in reference to the apnea detection service 406A.

The skin temperature estimation service 406N can execute a skin temperature estimation model 412N to determine a current skin temperature of the user for the sleep session and/or a change or average skin temperature of the user over the sleep session or over a threshold quantity of sleep sessions. The service 406N can request and execute the model 412N similarly as described above in reference to the apnea detection service 406A.

As described herein, the services 406A-N may run constantly (e.g., during a sleep session of the user) and request a respective model 412A-N when an initial condition occurs. The respective model 412A-N can be downloaded as a plugin at the remote computing system and wrapped with data for executing the model. The model is then transmitted to the requesting service via the messaging service 210 and the requesting service feeds sensor data received via the messaging service 210 as input to the model for execution. The requesting service then take output from the executed model and feeds it back to the messaging service 210 so that the output can be provided to the user and/or used in one or more other computations/determinations.

As an illustrative example, the sleep stages detection service 406C and the snore detection service 406D can each receive acoustic sensor signals from a bed system via the messaging service 210 as inputs to respective models 412C and 412D. However, the snore detection service 406D may also need to know times at which the user's snoring occurs during the sleep session. This timing information can be determined by the sleep stages detection service 406C and retrieved by the snore detection service 406D via the messaging service 210. To determine the sleep stages at the service 406C, for example, the service 406C can receive pressure data from the bed system via the messaging service 210 and provide this data to the model 412C. The model 412C can generate output indicating the user's heartrate at various timestamps. This output can be provided to the messaging service 210 and therefore accessible to be used as model input(s) by one or more other services, such as the snore detection service 406D. Thus, the snore detection service 406D can retrieve the timestamp output from the service 406C and provide that information as input to the snore detection model 412D to accurately determine when the user is snoring during the sleep session. Sometimes, data that is received from the sensors of the bed system and/or from any of the services 404A-N can be given a timestamp upon ingestion into the messaging service 210. These timestamps can then be used by any of the services 406A-N to correlate data provided by the sensors and/or outputs generated by the models 412A-N at any of the services 406A-N. Correlation of data using the timestamps can advantageously provide for improving accuracy of user information, insights, and/or metrics that are generated using the disclosed technology.

Some of the services 404A-N and 406A-N can be standalone computational services composed of a single-purpose service where a generated inference is part of the service. Illustrative examples of such services include the motion detection service 404B, the HRV computation service 404C, and the filtering and pre-processing services 402A-N. One or more other services may also be standalone computational services. Some of the services can also be wrapped computational model services as described herein. The wrapped model services can be composed from a model wrapper software/techniques and a respective model. The wrapped model services can advantageously allow for soft capabilities updates, where new models can be downloaded at such services without having to change the model wrapper software/techniques. Illustrative examples of the wrapped model services include, but are not limited to, a leak detection service (not depicted), the apnea detection service 406A, and the sleep stages detection service 406C.

FIG. 4C is a diagram of an example process 450 for invoking and executing the apnea detection model 412A at the apnea detection service 406A described in FIG. 4B. To begin, the apnea detection service 406A can transmit a request via the messaging service to request or read pressure data (452) of the user on the bed system. The pressure acquisition service 408A can receive pressure signals from pressure sensors of the user's bed system, as described in reference to FIG. 4A. The pressure acquisition service 408A can continuously add the pressure data (454) to the messaging service 210 to be ingested or read (456) by the apnea detection service 406A.

The apnea detection service 406A can then invoke the apnea detection model 412A and provide the pressure data as input to the model 412A (458). The model 412A can execute in the service 406A according to the available resources and compute power at the service 406A (on the edge) to generate output (460). The output can then be added to the messaging service 210 by the apnea detection service 406A (462). Then, one or more other services may ingest or read the model output from the messaging service 210 to make any other determinations described herein.

The process 450 can continuously be performed (e.g., loop through 452-462) until a service determines that the user has woken up from a current sleep session, the user has left the bed system for a threshold amount of time (e.g., the user got out of bed to start their day), and/or the user's sleep session ends. Moreover, although the process 450 is described in reference to executing the model 412A at the apnea detection service 406A, the process 450 can similarly be performed for one or more of the other services described throughout this disclosure.

Figure 5:
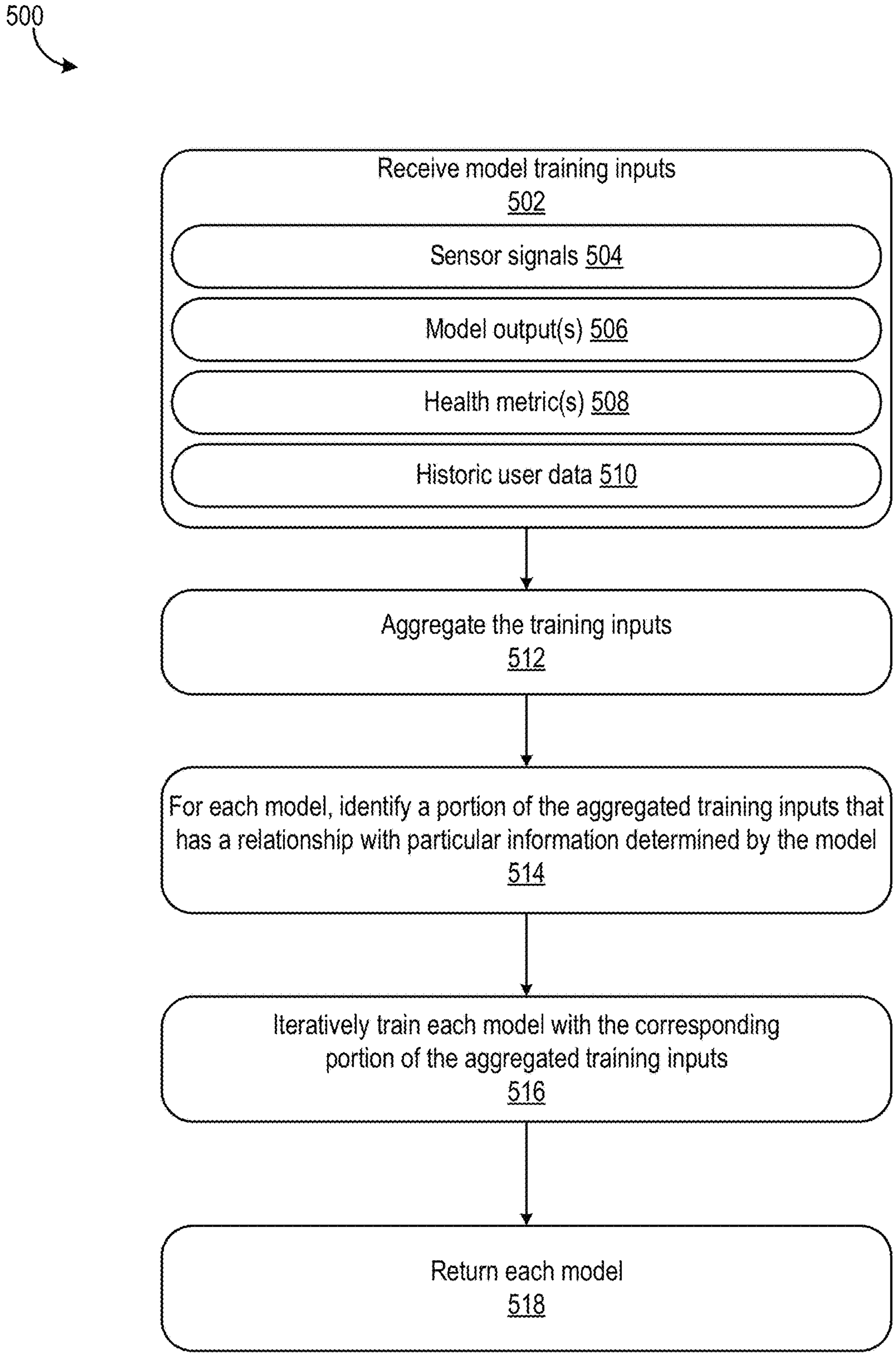
FIG. 5 is a flowchart of a process for training one or more edge-based models and/or remote-computing-based models for use in the disclosed techniques.

FIG. 5 is a flowchart of a process 500 for training one or more edge-based models and/or remote-computing-based models for use in the disclosed techniques. The process 500 can be performed by the remote computing system 106 described herein. For example, the remote computing system 106 can include a model training engine to perform the process 500. The process 500 can also be performed by one or more other computing systems. For illustrative purposes, the process 500 is described from the perspective of a computing system.

Referring to the process 500, the computing system receives model training inputs in block 502. The training inputs can include, but are not limited to, sensor signals (block 504), model output(s) (block 506), health metric(s) (block 508), and/or historic user data (block 510). The training inputs can be retrieved from a data store. The training inputs can be receives from one or more sensor signal acquisition services described in FIG. 4A. The training inputs can also be received from one or more sensors of the bed system. The training inputs may be received from one or more services executing on the edge or in the cloud/remotely. The training inputs can be received for a general population of users and used to train models for be deployed at many bed systems of many users. The training inputs can be received for a group of users sharing common traits or demographics (e.g., age, gender, disabilities/mobility, geographic location). Sometimes, the training inputs can be received for a particular user or bed system and used to train models that are used for determining information for a particular user or a particular bed system.

The computing system aggregates the training inputs in block 512. In other words, various different training inputs (e.g., signals) are pooled together to generate a more robust dataset for purposes of accurate model training.

For each model to be trained, the computing system identifies a portion of the aggregated training inputs that has a relationship with particular information that will be determined by the model (block 514). As described in reference to FIGS. 4A-C, each model is trained to determine a different type of information, insight, or metric about the user. The aggregated training inputs can include audio data, pressure data, previously detected snores, previously detected apnea, skin temperature estimations, HRV, HR, RR, and other types of data. A snore detection model, for example, may be trained with audio data, pressure data, and previously detected snores. In block 514, using one or more rules, for example, the computing system can determine that the snore detection model is trained with only the audio data, pressure data, and previously detected snores. Accordingly, the computing system can identify only this data from the aggregated training inputs and provide the identified data as inputs to the snore detection model for training purposes.

The computing system then iteratively trains each model with the corresponding portion of the aggregated training inputs in block 516. The computing system returns each model after training (block 518). The model can be stored in the data store, as described herein. The model can also be encrypted and stored or encrypted and transmitted over network(s) to a corresponding service operating on the edge. The model can be wrapped in a data object, as described further below. For example, the model training engine can pass the trained model to a model wrapping service at the computing system for wrapping and deployment of the model to a corresponding service. Sometimes, wrapping the model can be the same process as encrypting the model.

The process 500 can be repeated to iteratively train and improve the models. Accordingly, runtime model outputs/service determinations can be fed back into the process 500 as training inputs, then used to improve the accuracy of the respective models.

As an illustrative example, the process 500 can be used to train a snore detection model. Snore data, such as pressure signals and audio signals, associated with a general population of users can be pushed to/received at the computing system (e.g., in the cloud) for training the snore detection model to identify when a user is snoring. Once the model is trained an validated, the model can be wrapped and deployed to a snore detection service operating on the edge so that during runtime, snore detections and bed system adjustments can be performed on the edge at the bed system in real-time.

Figure 6:
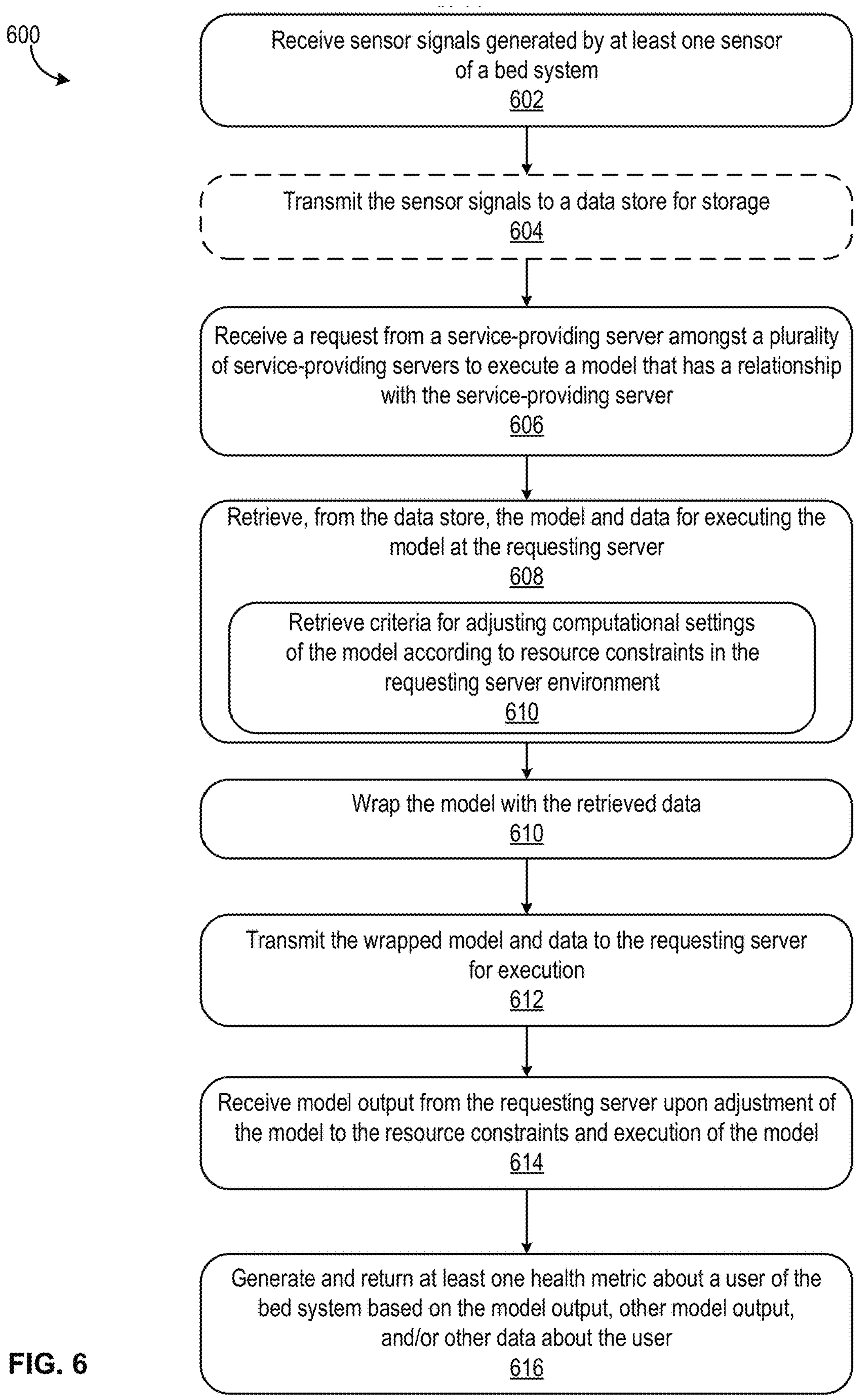
FIG. 6 is a flowchart of a process for generating health metrics and information about a user based on processing data collected at a bed system.

FIG. 6 is a flowchart of a process 600 for generating health and/or wellness metrics and information about a user based on processing data collected at a bed system. The process 600 can be performed by the remote computing system 106 described herein. The process 600 can also be performed by one or more other computing systems. For illustrative purposes, the process 600 is described from the perspective of a computing system.

Referring to the process 600 in FIG. 6, the computing system can receive sensor signals generated by at least one sensor of a bed system in block 602. More particularly, a messaging service of the computing system can receive the generated signals from the at least one sensor. The at least one sensor can include a pressure sensor and the sensor signals can be pressure signals. The at least one sensor can include an audio sensor and the sensor signals can be audio signals. The at least one sensor can include a temperature sensor and the sensor signals can be temperature signals. The at least one sensor can include an array of temperature signals and the sensor signals can be temperature signals. The at least one sensor can include a load cell and the sensor signals can be load cell signals. The at least one sensor can also include a combination of any one or more of the group including: pressure sensors, audio sensors, temperature sensors, and load cells.

The computing system can optionally transmit the sensor signals to a data store for storage in block 604. The messaging service can, for example, transmit the received sensor signals to the data store.

In block 606, the computing system can receive a request from a service-providing service amongst a plurality or group of service-providing servers (e.g., the services described herein) to execute a model that has a relationship with the service-providing server. The service-providing servers can be any of the independently run services described throughout this disclosure. For example, a model wrapping service of the computing system can receive, from a service-providing server amongst the plurality of service-providing servers via the messaging service, a request to execute a model that has a relationship with the service-providing server.

The plurality of service-providing servers each can have one or more processors and memory and be in communication over a network with other components of the bed system. Each of the plurality of service-providing servers can run independently of each other and execute a model for determining particular sleeper information based at least in part on the sensor signals generated by the at least one sensor. A first subset of the plurality of service-providing servers can run in a cloud-based system, such as at the computing system, and a second subset of the plurality of service-providing servers can run on the edge at an edge computing device. The edge computing device can be a controller and/or a pump of the bed system, in some implementations. The edge computing device can control the one or more components of the bed system. The edge computing device can also process at least a portion of the sensor signals generated by the at least one sensor. For example, as described in reference to FIGS. 4A-B, one or more filtering and/or pre-processing service-providing servers can be executed on the edge to process the sensor signals before providing the signals to the plurality of service-providing servers. Refer to FIGS. 1-4 for further discussion about the service-providing servers.

The first subset of the plurality of service-providing servers can include, but are not limited to, an illness detection service-providing server. The illness detection service-providing server can be configured to execute an illness detection model having been trained to determine, over a threshold quantity of sleep sessions of the user, whether the user developed an illness. The illness detection model can be trained to receive, as inputs, historic user health data, the generated sensor signals, and model output from one or more of the plurality of service-providing servers, process the received inputs, and generate, as a result of processing the inputs, output indicating a likelihood that the user developed the illness.

The second subset of the plurality of service-providing servers can include, but is not limited to: a motion detection service-providing server, a respiratory rate detection service-providing server, a heartrate detection service-providing server, a heartrate variability computation service-providing server, a time-to-fall-asleep computation service-providing server, a bed presence detection service-providing server, a snore detection service-providing server, and a snore response service-providing server. As an illustrative example, the snore detection service-providing server can run at the edge computing device and can: receive, from an acoustic sensor of the bed system, acoustic signals while the user rests on the bed system, pass the acoustic signals to a snore detection model that is executed at the snore detection service-providing server and configured to generate output indicating whether the user snores while the user rests on the bed system, and transmit the snore detection model output to the messaging service of the computing system for further processing. As another example, the sleep stage service-providing server can: receive, from a pressure sensor of the bed system, pressure signals while the user rests on the bed system, pass the pressure signals to a sleep stage model that is executed at the sleep stage service-providing server and configured to generate output indicating at least heartrate of the user at predetermined time intervals while the user rests on the bed system, and transmit the sleep stage model output to the messaging service of the computing system for further processing. Sometimes, the computing system can: transmit, to the snore detection service-providing server via the messaging service, the snore detection model output and a portion of the sleep stage model output. The portion of the sleep stage model output may include the predetermined time intervals. The snore detection service-providing server can also correlate identified snore detections in the snore detection model output with the predetermined time intervals to determine when the user snores while resting on the bed system.

Blocks 602, 604, and 606 can be performed in one or more other orders. For example, the computing system may receive the request for a model from a service-providing server (block 606) before receiving the sensor signals (block 602) and/or before storing the sensor signals in the data store (block 604). Sometimes, for example, the computing system may not receive the sensor signals in block 602 and instead the sensor signals may be transmitted directly from the at least one sensor of the bed system to one or more of the plurality of service-providing servers. As another example, a service-providing server may first receive the sensor signals then transmit the sensor signals to the computing system (e.g., in block 602) and/or store the signals in the data store (block 604). One or more other variations of blocks 602, 604, and 606 are also possible.

The computing system can accordingly retrieve, from the data store via the messaging service, the model and data for executing the model at the requesting server (block 608). The data can include one or more of the signals that were stored in the data store in block 604. Sometimes, the sensor signals can be transmitted directly from the at least one sensor, via the messaging service, to the requesting service-providing server.

As part of block 608, the computing system can retrieve criteria for adjusting computational settings of the model according to resource constraints in the requesting server environment (block 610). After all, computation and processing resources are limited on the edge. Therefore, the model can be parameterized using the criteria so that the model automatically adjusts its parameters when it runs on the edge to adjust to this computational environment. In fact, the request that is received in block 606 can include an indication or other information about the environment in which the service-providing server is operating, which can be used by the computing system to retrieve the appropriate criteria to adjust the model for proper and efficient execution at the server. For example, the request to execute the model can include information indicating an environment of the requesting service-providing server, the environment being one of the remote computing system or the edge computing device. The environment of the requesting service-providing server can be defined based on whether the requesting service-providing server is part of the first subset of the plurality of service-providing servers run in the computing system or the second subset of the plurality of service-providing servers run at the edge computing device. The retrieved data for executing the model at the requesting service-providing server can therefore include the criteria for adjusting computational settings of the model based on the environment of the requesting service-providing server so that the retrieved model can, based on whether the criteria is satisfied, automatically adjust the computational settings of the model to parameterize the model for deployment in the environment of the requesting service-providing server.

The computing system can wrap the model with the retrieved data in block 610. Sometimes, for example, the messaging service can load, based on the retrieved data, the model as a plugin at the computing system and then wrap the plugin model. The model can be wrapped into a data object, which can include the model and instructions that, when executed at the requesting service-providing server, cause the model to automatically adjust execution parameters based on resource constraints of the edge computing environment where the requesting server runs.

In block 612, the computing system can transmit the wrapped model and data to the requesting server for execution.

The computing system may also receive model output from the requesting server upon adjustment of the model to the resource constraints and execution of the model by the requesting server (block 614).

The computing system can then generate and return at least one health metric about a user of the bed system based on the model output, other model output, and/or other data about the user (block 616). The at least one health metric can be returned for presentation in a graphical user interface (GUI) display of a computing device of the user. The at least one health metric can be returned based on a determination made by the computing system or one or more service-providing servers operating on the edge that a sleep session of the user has ended.

In block 616, an aggregator of the computing system can receive, via the messaging service, the model output. The aggregator can be configured to generate the at least one health metric about the user based on correlating the model output with at least one of other model outputs or other data about the user. The at least one health metric can be a determination of the user's vitals at one or more time intervals during a sleep session of the user. The at least one health metric can also be one or more types of wellness metrics. The at least one health metric can be generated using one or more rules for correlating different types of model outputs to determine the health metric. Sometimes, the at least one health metric can be generated using a model having been trained to correlate different types of model outputs to determine the health metric. As an illustrative example, the computing system can pass the snore detection model output and the sleep stage model output to the aggregator, and the aggregator can correlate the snore detection model output with the sleep stage model output to determine a health condition of the user. Determining the health condition of the user may include applying an aggregation model to the snore detection model output and the sleep stage model output, the aggregation model having been trained to correlate data and determine health conditions of users based on the correlated data.

As another illustrative example of block 616, the computing system can receive the model output (e.g., first health information about the user) from one or more of the requesting service-providing servers. The computing system can then determine the at least one health metric (e.g., second health information about the user) for the user based on applying a model to the received sensor signals (block 602) and the model output. The model can be trained and configured to execute in a service that runs at the computing system (e.g., in the cloud, remote from the bed system). The computing system can then return instructions for presenting at least a portion of the model output from the requesting service-providing server(s) and the at least one health metric to the user at the user's computing device. The instructions, when executed by the computing device of the user, can cause the computing device to output the at least portion of the model output and the at least one health metric in a GUI display of the computing device (e.g., in a mobile application that is launched by the user and/or automatically at the computing device once a sleep session of the user ends).

Although the process 600 is described in reference to one requesting service-providing server, the process 600, or one or more blocks in the process 600, can also be performed for each independently run service-providing server that makes determinations about the user's sleep and/or health during a sleep session of the user. Therefore, the process 600 can be performed in parallel, simultaneously and/or multiple times throughout the sleep session of the user (and sometimes in series) to ensure that the servers are executing efficiently to generate user information in real-time or near real-time.

Figure 7:
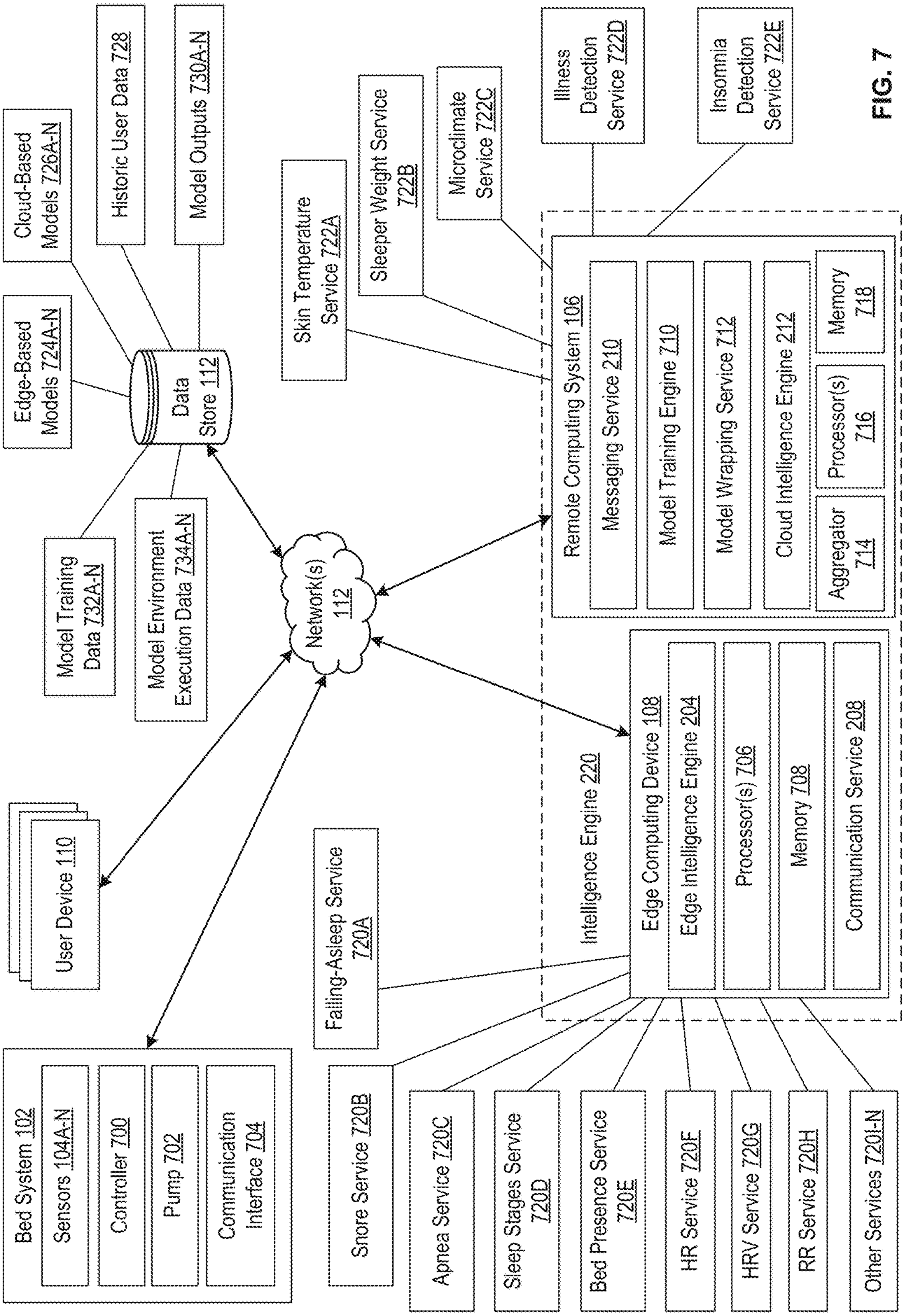
FIG. 7 is a system diagram illustrating one or more system components that can be used to perform the techniques described herein.

FIG. 7 is a system diagram illustrating one or more system components that can be used to perform the techniques described herein. The bed system 102, user device 110, data store 112, edge computing device 108, and remote computing system 106 can communicate via the network(s) 112, as described in reference to FIG. 1. As shown in FIG. 7 and described in reference to FIG. 2, the edge computing device 108 and the remote computing system 106 can be part of an intelligence engine 220. The edge computing device 108 can operate in an edge computing environment. Sometimes, the edge computing device 108 can be part of the bed system 102. Sometimes the edge computing device 108 can be the user device 110. The remote computing system 106 can operate in a computing environment that is remote from the bed system 102, such as a cloud-based computing environment. Accordingly, the edge computing device 108 and the remote computing system 106 can have different resource constraints that impact how the models described herein are adapted for execution.

The bed system 102 can include at least the sensors 104A-N described herein, a controller 700, a pump 702, and a communication interface 704. The controller 700 can be configured to control one or more components of the bed system 102. The controller 700 can be integrated into the bed system 102 and/or a remote controller. The controller 700 can also make one or more determinations described herein. Sometimes, the controller 700 can be the edge computing device 108. The controller 700 can, in some implementations, automatically adjust or articular a foundation of the bed system 102 based on one or more determinations that are made at the edge computing device 108. As another example, the controller 700 can automatically adjust a microclimate at a top surface of the bed system 102 based on one or more determinations made at the intelligence engine 220. The controller 700 can also adjust a firmness of the bed system 102 based on one or more determinations that are made at the edge computing device 108. Moreover, the controller 700 can automatically control one or more components of the bed system 102 based on user input that is received from the user of the bed system 102 at the user device 110. The user input can indicate one or more adjustments to be made to one or more components of the bed system 102.

The pump 702 can be configured to adjust an amount of airflow that enters or exits air chambers of the bed system 102. Accordingly, the pump 702 can be used to adjust a firmness of the bed system 102. The pump 702 can receive control operations from the controller 700, the user device 110, and/or the edge computing device 108. Sometimes, the pump 702 and the controller 700 can be a same component or part of a same component of the bed system 102. The communication interface 704 can provide communication over the network(s) 112 between the components of the bed system 102 and the other components described herein.

The edge computing device 108 can include at least the edge intelligence engine 204 described herein, processor(s) 706, memory 708, and the communication service 208 described herein. The edge intelligence engine 204 can include one or more services 720A-N that are independently run and configured to request and execute corresponding edge-based models 724A-N on the edge. The services 720A-N therefore can be any of the edge-based services described throughout this disclosure. For example, the services 720A-N can include a falling-asleep service 702A, a snore service 720B, an apnea service 720C, a sleep stages service 720D, a bed presence service 720E, an HR service 720F, an HRV service 720G, a RR service 720H, and any other services 720I-N. Determinations or model outputs at each of the services 720A-N can be transmitted to the data store 112 and stored as model outputs 730A-N. Any of the determinations or model outputs can also be transmitted to the user device 110 for presentation in a GUI display to the user and/or to the remote computing system 106 for further processing. Refer to FIGS. 3A, 3B, 4A, and 4B for further discussion about the services 720A-N.

The remote computing system 106 can include at least the messaging service 210 described herein, a model training engine 710, a model wrapping service 712, the cloud intelligence engine 212 described herein, an aggregator 714, processor(s) 716, and memory 718. In brief, the cloud intelligence engine 212 can include one or more services 722A-N, which can be independently run and configured to execute corresponding cloud-based models 726A-N. The services 722A-N therefore can be any of the remote cloud-based services described throughout this disclosure. For example, the services 722A-N can include a skin temperature service 722A, a sleeper weight service 722B, a microclimate service 722C, an illness detection service 722D, and an insomnia detection service 722F. One or more other services may also run in the remote computing system 106 to determine other user health and/or sleep metrics/insights. Determinations or model outputs at each of the services 722A-E can be transmitted to the data store 112 and stored as the model outputs 730A-N. Any of the determinations or model outputs can also be transmitted to the user device 110 for presentation in a GUI display to the user and/or used by one or more other services 722A-E to generate additional insights/information about the user. Refer to FIGS. 3A, 3B, 4A, and 4B for further discussion about the services 722A-F.

The model training engine 710 can be configured to generate, train, and continuously improve the models 724AN-N and 726A-N. As described in reference to the process 500 in FIG. 5, the engine 710 can retrieve model training data 732A-N from the data store 112. The engine 710 can also retrieve historic user data 728 from the data store 112. The engine 710 can aggregate the data 732A-N and 728 and then identify portions of the aggregated data to be used for training each model of the models 724A-N and 726A-N. The engine 710 can train the models 724A-N and 726A-N accordingly, then store the models 724A-N and 726A-N in the data store 112 for later retrieval when a corresponding service 720A-N and/or 722A-N requests a model for runtime execution.

The model wrapping service 712 can be configured to receive requests for models from one or more of the services described herein. For example, the service 712 can receive, during a sleep session of the user, a request for at least one of the edge-based models 724A-N from at least one corresponding service 720A-N operating on the edge at the edge computing device 108. Accordingly, the service 712 can retrieve, from the data store 112, the at least one edge-based model 724A-N that has a relationship with the requesting service 720A-N and corresponding model environment execution data 734A-N. The model environment execution data 734A-N can indicate one or more resource constraints and/or model parameter adjustments to be made for proper and efficient execution of the retrieved model in the execution environment. The service 712 can wrap the retrieved model along with instructions associated with the corresponding model environment execution data 734A-N into a data object. Wrapping this data into the data object can include encryption techniques, as described in reference to FIG. 9. As a result, the data object can be securely transmitted over the network(s) 112 to the requesting service at the edge computing device 108. Sometimes, the service 712 can also wrap the retrieved model and the instructions for model parameterization/execution with one or more of the sensor signals generated by the sensors 104A-N, one or more of the model outputs 730A-N, and/or the historic user data 728, all of which may be used by the requesting service as inputs to the wrapped model.

The aggregator 714 can be configured to aggregate or combine one or more determinations from the services 720A-N and/or 722A-N to generate health and sleep metrics about the user, as described throughout this disclosure. Refer to the process 800 in FIGS. 8A-B for further discussion.

The user device 110 can be any type of computing device described herein, including but not limited to a mobile device, mobile phone, smartphone, tablet, laptop, wearable device, and/or computer. The user device 110 can include input devices, such as a microphone, keyboard, and/or touch screen, configured to receive feedback and/or input from the user. The user device 110 can also include output devices, such as speakers, the touch screen, and/or other displays for presenting information to the user. As described herein, for example, the user device 110 can present a mobile application in a GUI display. The user can provide input in the mobile application to view information about their current sleep session and/or prior sleep session(s). The user can provide input in the mobile application to control one or more components of the bed system 102. The user can provide input in the mobile application to view one or more sleep and/or health metrics, insights, or other information that is determined for the user based on the disclosed techniques. One or more other interactive capabilities are also possible with the mobile application presented at the user device 110 to provide the user with improved insights and control of their sleep environment, sleep experience, and/or overall health.

Figure 8A:
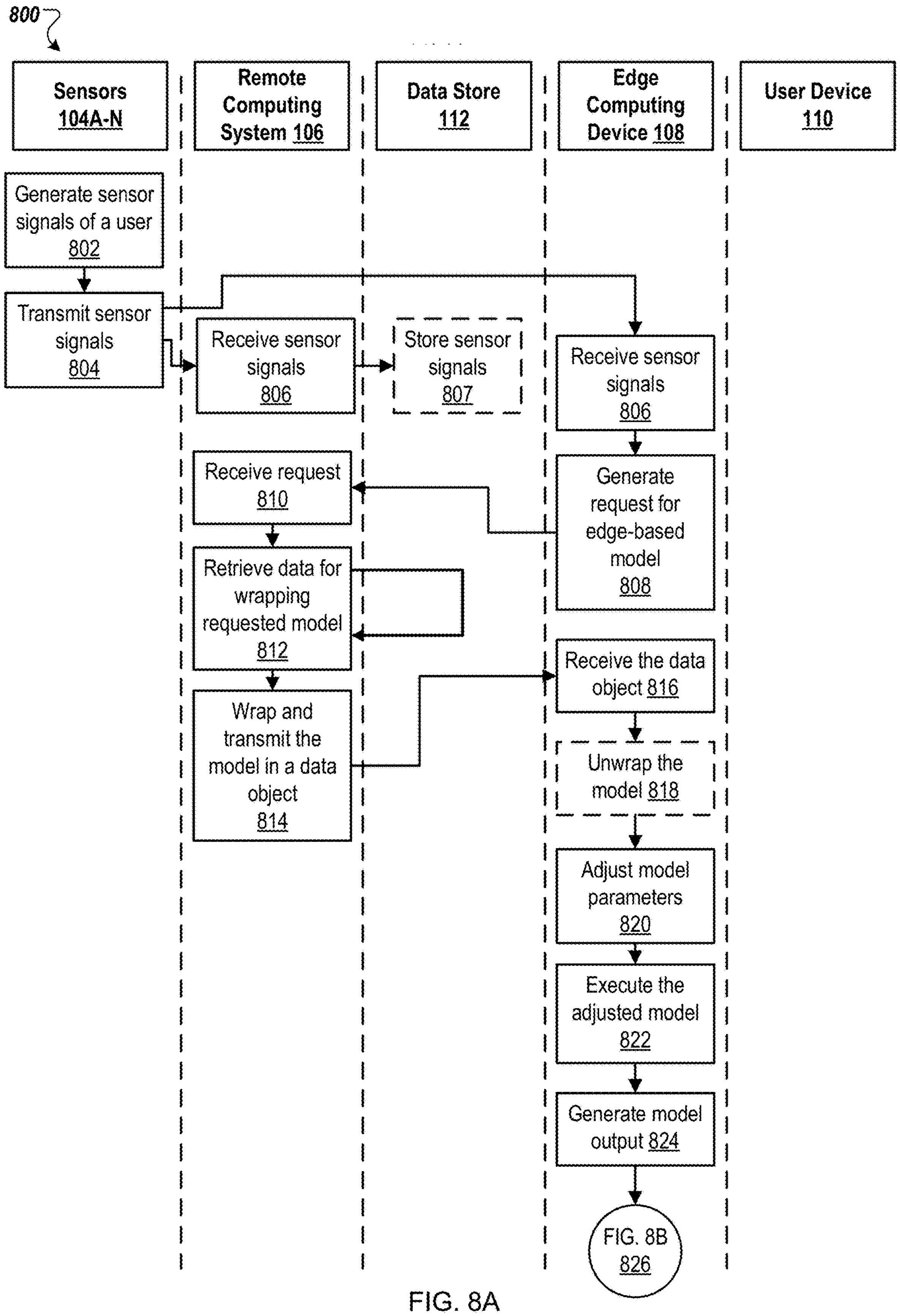
FIGS. 8A-B is a swimlane diagram of a process for generating health metrics and information about a user based on processing data collected at a bed system.
Figure 8B:
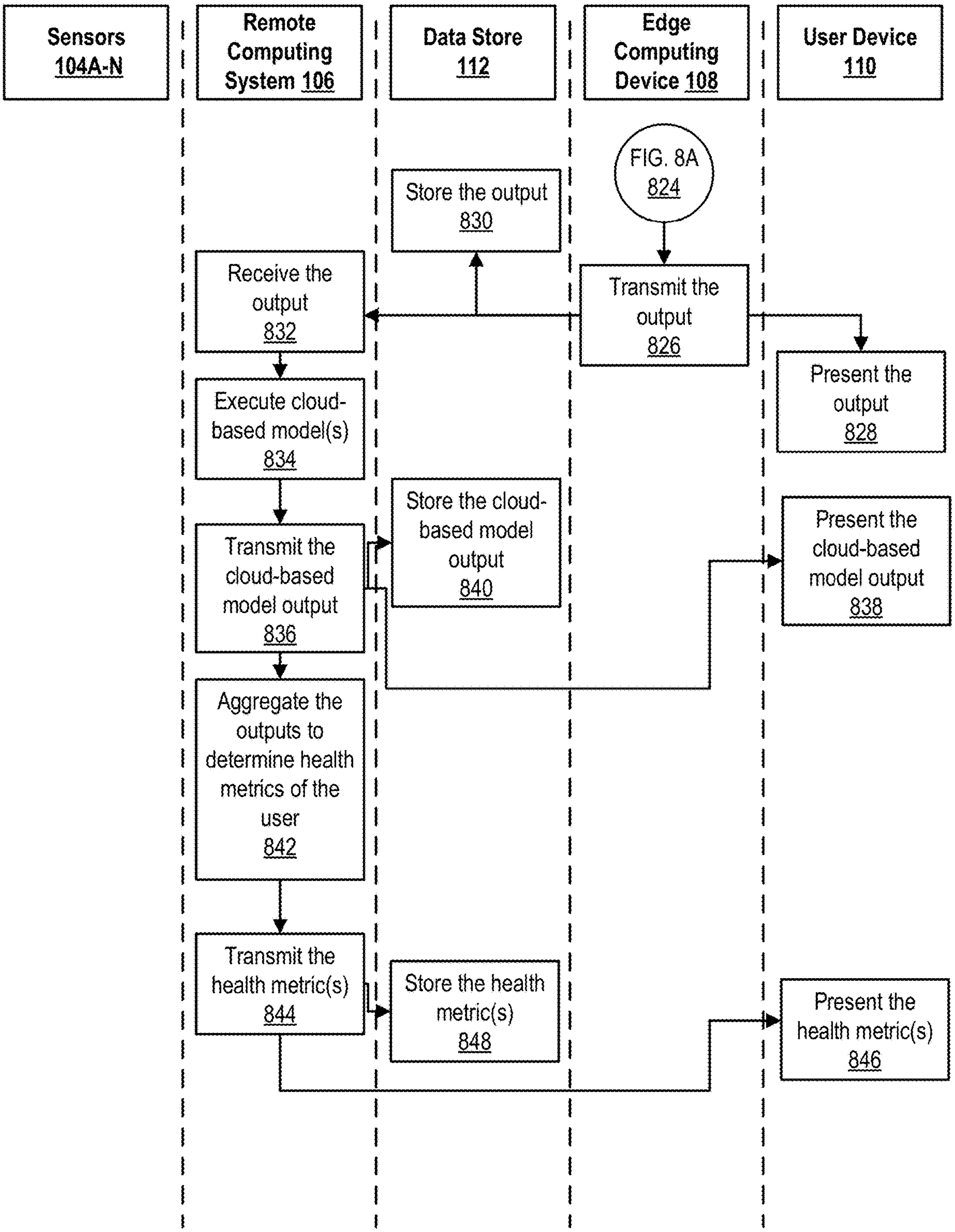

FIGS. 8A-B is a swimlane diagram of a process 800 for generating health metrics and information about a user based on processing data collected at a bed system. The process 800 can be performed by components described herein including but not limited to the sensors 104A-N of the bed system 102, the remote computing system 106, the data store 112, the edge computing device 108, and the user computing device 110. One or more other components may also be used to perform one or more blocks in the process 800.

Referring to the process 800 in both FIGS. 8A-B, the sensors 104A-N can generate sensor signals of a user resting on the bed system in block 802. Refer to FIGS. 1-7 for further discussion. The sensors 104A-N can transmit the sensor signals in block 804 to the remote computing system 106 and/or the edge computing device 108, both of which may receive the signals in block 806. In some implementations, before transmitting the generated sensor signals, the bed system and/or the sensors 104A-N can be configured to anonymize the generated sensor signals and form a client authentication process to ensure that data and other information is securely transmitted between the components described herein.

Sometimes, the sensors signals can be transmitted to the remote computing system 106, which then transmits the signals to the edge computing device 108. Sometimes, the signals can be transmitted to the edge computing device 108, which then transmits the signals or a portion of the signals to the remote computing system 106 at a later time in the process 800. The edge computing device 108 can, for example, receive, from the at least one sensor, the sensor signals in real-time or near real-time as the sensor signals are generated by the at least one sensor during the sleep session of the user. Sometimes, as described herein, the edge computing device 108 can filter and/or pre-process the received signals.

The remote computing system 106 can optionally store the sensor signals in block 807, as described herein.

The edge computing device 108 can generate a request for an edge-based model in block 808. More particularly, a service (e.g., a service-providing server as described in FIG. 6) running at the edge computing device 108 can generate the request for a model that has a relationship with the service. The request can be transmitted to and received at the remote computing system 106 in block 810. A plurality of services can be running on the edge in order to continuously monitor sleep and/or health conditions of the user in real-time or near real-time throughout a current sleep session.

As an illustrative example, the service can request an edge-based model that may be used to determine when the user falls asleep during the sleep session and when the user stays asleep during the sleep session. Another service can request an edge-based model that may be used to detect when the user or a partner in the bed system is snoring and automatically adjust a respective side of the bed system based on the snore detection. Another service can request an edge-based model that may be used to detect sleep apnea of the user during the sleep session. Another service can request an edge-based model that may be used to detect sleep stages of the user during the sleep session. Another service can request an edge-based model that may be used to detect bed presence of the user resting on the bed system. Another service can request an edge-based model that may be used to determine a heartrate of the user throughout the sleep session. Another service can request an edge-based model that may be used to determine a heartrate variability of the user throughout the sleep session. Another service can request an edge-based model that may be used to determine a respiratory rate of the user throughout the sleep session. One or more other services and edge-based models are also possible, as described throughout this disclosure.

The remote computing system 106 can retrieve data from the data store 112 for wrapping the requested model in block 812. The data can include instructions for parameterizing the model to operate efficiently and accurately in computing environments having different resource constraints. The data can also include instructions for encrypting the model and associated data for secure transfer between the remote computing system 106 and the edge computing device 108.

The remote computing system 106 can then wrap and transmit the model in a data object to the edge computing device 108 (block 814). Wrapping the model can include encrypting the model, as described in FIG. 9. For example, the remote computing system 106 can transmit the data object to the edge computing device 108 using mutual authentication techniques.

The edge computing device 108 can receive the data object in block 816. More particularly, the requesting service can receive the data object.

Optionally, the edge computing device 108, or the particular requesting service, can unwrap the model in block 818. Unwrapping the model can include decrypting the model, as described in FIG. 10.

The edge computing device 108, or the requesting service more particularly, can automatically adjust the model parameters in block 820 based on data in the data object.

The adjusted model can then be executed at the requesting service at the edge computing device 108 (block 822). For example, the requesting service at the edge computing device 108 can determine a first set of sleeper information for the sleep session of the user of the bed system based on applying the adjusted model to the received sensor signals. The first set of sleeper information can include intra-sleep information about the user during the sleep session, as described further in reference to FIG. 3A. The first set of sleeper information can be determined at predetermined time intervals during the sleep session of the user. The predetermined time intervals can be every second during the sleep session. The predetermined time intervals can be any other amount of time, including but not limited to 0.5 second intervals, 3 second intervals, 5 second intervals, 15 second intervals, etc. Sometimes, the requesting service can continuously determine the first set of sleeper information throughout the sleep session of the user and/or until a service running on the edge determines, based on the sensor signals generated by the sensors 104A-N, that the sleep session ends and/or the user exits the bed system. In some implementations, the received sensor signals and the first set of sleeper information can be temporarily stored in local memory at the edge computing device 108 until transmitted to the remote computing system 106. Then, transmitting the sensor signals and the first set of sleeper information to the remote computing system 106 can include removing them from storage in the local memory of the edge computing device 108. The remote computing system 106 can then decrypt the sensor signals and/or the first set of sleeper information upon receiving and ingesting this transmitted information from the edge computing device 108.

Sometimes, as described herein, the plurality of services can each request a respective model at same or similar times in block 808. The remote computing system 106 can wrap each of the models separately and transmit the wrapped models to the corresponding services. Then, each of the services can execute their respective models. Output from the models can be the first set of sleeper information.

The edge computing device 108, or the requesting service more particularly, can generate output based on executing the model in block 824.

The edge computing device 108 can then transmit the output in block 826 to the remote computing system 106, the data store 112, and/or the user device 110. The data store 112 can store the output in block 830. The user device 110 can present the output in a GUI display to the user (block 828). The remote computing system 106 can receive or ingest the output (block 832). Sometimes, the edge computing device 108 can also transmit, to the remote computing system 106 and/or the data store 112, one or more of the sensor signals with the model output in block 826.

The remote computing system 106 can then execute one or more cloud-based models using at least some of the output received in block 832 and/or the sensor signals received in block 806 (block 834). Executing the cloud-based model(s) can include generating output about one or more health metrics, insights, or other user information for the user of the bed system. For example, a second set of sleeper information for the user of the bed system can be determined based on applying at least one cloud-based model to the received sensor signals and the first set of sleeper information. The cloud-based model can be configured to execute according to resource constraints of the cloud-based remote computing system 106, and the resource constraints of the remote computing system 106 can be different than the resource constraints of the edge computing device 108, as described throughout this disclosure.

Still referring to block 834, the second set of sleeper information can include inter-sleep information about the user for at least one of: each sleep session or a threshold quantity of sleep sessions. Sometimes, the remote computing system 106 can receive the generated sensor signals once the sleep session ends and determine the second set of sleeper information after the sleep session or a threshold amount of time after the sleep session of the user. One or more services operating at the remote computing system 106 and/or the edge computing device 108 can determine that the sleep session ended based on identifying a sleep-to-wake transition of the user at the bed system and/or a bed exit event at the bed system.

The cloud-based model that is executed in block 834 can be configured to determine a skin temperature of the user for the sleep session. One or more other cloud-based models can be configured to determine a weight of the user for the sleep session, determine an in-bed microclimate for the sleep session, determine illness symptoms of the user for the sleep session, detect insomnia of the user for the sleep session, and/or determine whether the user has an illness or disease over a threshold quantity of sleep sessions.

The remote computing system 106 can transmit the cloud-based model output in block 836 to the data store 112 and/or the user device 110. For example, the data store 112 can store the output in block 840 for later retrieval, further processing, and/or presentation to the user at the user device 110. The first and second sets of sleeper information can be stored in associated with the user of the bed system. The user device 110 can present the cloud-based model output in block 838 in the GUI display.

The remote computing system 106 can additionally or alternatively aggregate the outputs from the edge-based model(s) and/or the cloud-based model(s) to determine health metrics or other insights of the user (block 842). As described herein, the remote computing system 106 can include an aggregator service that can be configured to determine a sleep metric for the user of the bed system based on applying one or more rules for aggregating the first and second sets of sleeper information. The sleep metric can be a sleep quality score for the sleep session. The sleep metric can be a restful time metric for the sleep session. The sleep metric can be an in/out-of-bed pattern for the sleep session of the user. The sleep metric can be a change in body weight of the user over a threshold quantity of sleep sessions. The sleep metric can be a personalized insight to improve overall sleep quality for the user over a threshold quantity of sleep sessions. The sleep metric can additionally or alternatively be an apnea risk assessment of the user over a threshold quantity of sleep sessions.

The remote computing system 106 then transmits the health metric(s) in block 844 to the data store 112 and/or the user device 110. The data store 112 can store the health metric(s) for later retrieve, use in further processing, and/or presentation to the user. The user device 110 can present the health metric(s) in the GUI display to the user in block 846.

In some implementations, in blocks 836 and/or 844, the remote computing system 106 can generate and return instructions for presenting the first and second sets of sleeper information to the user of the bed system. The instructions, when received and then executed by the user device 110, can cause the user device 110 to output at least a portion of the first and second sets of sleeper information for the user in the GUI display of the user device 110 responsive to determining that the sleep session ended, that the user has left the bed system, and/or that the user requests to view at least some of the first and second sets of sleeper information at their device 110.

FIG. 9 is a diagram illustrating an example process 900 for encrypting models to transmit to and deploy at an edge computing device, such as the edge computing device 108. Mutual authentication techniques can be used to protect models from unauthorized access and/or modification. The process 900 is described from the perspective of the remote computing system 106. However, one or more operations in the process 900 can be performed by one or more other components, computing systems, and/or cloud-based computing systems.

Referring to the process 900, an installer 904 of the remote computing system 106 can read a model file or files from volatile storage 902 (operation 910). Operation 910 can be performed in response to receiving a request from a service for a model that has a relationship with the service. The service can be operating on the edge at the edge computing device and may execute the model during runtime, in real-time during a sleep session of the a user of a bed system, as described herein. Moreover, the model file may not be stored in persistent memory if unencrypted in order to protect the model file from security risks or otherwise being compromised.

The remote computing system 106 can loop through initializing an encryption module. For example, the installer 904 can read a black blob (operation 912) from persistent storage 906 of the remote computing system 106. The black blob is an example data encryption key that can be encrypted with HW-generated keys.

If the black blob read is a success, the installer 904 can communicate with a CAAM driver 908 of the remote computing system 106 to encrypt the model file (operation 914). The black blob can be used by the CAAM driver 908 to encrypt and decrypt user-provided date, such as model files to be executed on the edge. The installer 904 can then read the encrypted model file (operation 916) and store the encrypted model file (operation 918) in the persistent storage 906.

Referring back to operation 912, if no black blob is found during the read, then the installer 904 can communicate with the CAAM driver 908 to encapsulate a black key (operation 920). The installer 904 can then read the black blob (operation 922) and store the black blob (operation 924) in the persistent storage 906.

Once the encrypted model file is stored (operation 918) and/or the black blob is stored (operation 924), the encryption process 900 is complete and the model can be securely transmitted to the requesting service (at a current time or at another time when the service requests the model).

FIG. 10 is a diagram illustrating an example process 1000 for decrypting models at an edge computing device for edge-based execution. One or more operations in the process 1000 can be performed by components of the remote computing system 106 and/or the edge computing device 108, as described below.

Referring to the process 1000, the edge intelligence engine 204 of the edge computing device can read an encrypted model file (operation 1004) that was stored in the persistent storage 906 of the remote computing system (refer to FIG. 9). The edge intelligence engine 204 can also read the black blob of FIG. 9 from the persistent storage 906 (operation 1006).

If the black blob read is successful, the edge intelligence engine 204 can communicate with the CAAM driver 908 of the remote computing system 106 to decrypt the model file (operation 1008) and then read the model file (operation 1010). The edge intelligence engine 204 can also create a model interpreter instance in operation 1012, which can include generating an instance of the model based on the decrypted model file, for execution in the model environment (e.g., a particular service requesting the model).

The edge intelligence engine 204 (or more specifically, the particular requesting service) can then invoke the model with data received from at least one sensor of the bed system, as described herein (operation 1014). The edge intelligence engine 204 can loop through executing the model so long as the edge intelligence engine 204 determines one or more user health and/or sleep metrics/insights/information using the model output and/or one or more conditions are satisfied (e.g., the model has run with all of the received data, a threshold amount of time has passed during which the model runs).

Referring back to operation 1006, if the edge intelligence engine 204 reads the black blob but no black blob is identified or found, the edge intelligence engine 204 can report an error (operation 1016) to a logger 1002.

Figure 11:
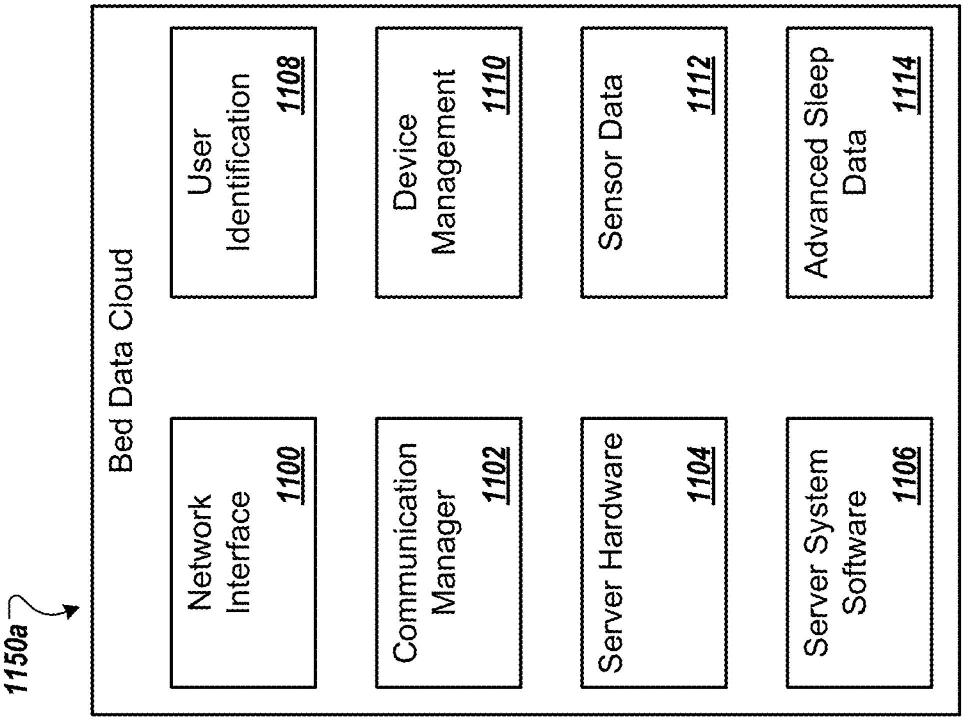

FIG. 11 is a block diagram of an example bed data cloud service 1150*a* used in a data processing system associated with a bed system, such as the bed system 102 described herein. Here, the bed data cloud service 11510*a* is configured to collect sensor data and sleep data from a particular bed, and to match the data with one or more users that used the bed when the data was generated.

The bed data cloud service 1150*a* includes a network interface 1100, a communication manager 1102, server hardware 1104, and server system software 1106. The bed data cloud service 1150*a* is also shown with a user identification module 1108, a device management 1210 module, a sensor data module 1210, and an advanced sleep data module 1114. The network interface 1100 includes hardware and low level software to allow hardware devices (e.g., components of the service 1150*a*) to communicate over networks (e.g., with each other, with other destinations over the Internet). The network interface 1100 can include network cards, routers, modems, and other hardware. The communication manager 1102 generally includes hardware and software that operate above the network interface 1100 such as software to initiate, maintain, and tear down network communications used by the service 1150*a* (e.g., TCP/IP, SSL or TLS, Torrent, and other communication sessions over local or wide area networks). The communication manager 1102 can also provide load balancing and other services to other elements of the service 1150*a*. The server hardware 1104 generally includes physical processing devices used to instantiate and maintain the service 1150*a*. This hardware includes, but is not limited to, processors (e.g., central processing units, ASICs, graphical processers) and computer readable memory (e.g., random access memory, stable hard disks, tape backup). One or more servers can be configured into clusters, multi-computer, or datacenters that can be geographically separate or connected. The server system software 1106 generally includes software that runs on the server hardware 1104 to provide operating environments to applications and services (e.g., operating systems running on real servers, virtual machines instantiated on real servers to create many virtual servers, server level operations such as data migration, redundancy, and backup).

The user identification 1108 can include, or reference, data related to users of beds with associated data processing systems. The users may include customers, owners, or other users registered with the service 1150*a* or another service. Each user can have a unique identifier, user credentials, contact information, billing information, demographic information, or any other technologically appropriate information.

A device manager 1110 can include, or reference, data related to beds or other products associated with data processing systems. The beds can include products sold or registered with a system associated with the service 1150*a*. Each bed can have a unique identifier, model and/or serial number, sales information, geographic information, delivery information, a listing of associated sensors and control peripherals, etc. An index or indexes stored by the service 1150*a* can identify users associated with beds. This index can record sales of a bed to a user, users that sleep in a bed, etc.

Sensor data 1112 can record raw or condensed sensor data recorded by beds with associated data processing systems. For example, a bed's data processing system can have temperature, pressure, motion, audio, and/or light sensors. Readings from these sensors, either in raw form or in a format generated from the raw data (e.g. sleep metrics), can be communicated by the bed's data processing system to the service 1150*a* for storage in the sensor data 1112. An index or indexes stored by the service 1150*a* can identify users and/or beds associated with the sensor data 1112.

The service 1150*a* can use any of its available data (e.g., sensor data 1112) to generate advanced sleep data 1114. The advanced sleep data 1114 includes sleep metrics and other data generated from sensor readings (e.g., health information). Some of these calculations can be performed in the service 1150*a* instead of locally on the bed's data processing system because the calculations can be computationally complex or require a large amount of memory space or processor power that may not be available on the bed's data processing system. This can help allow a bed system to operate with a relatively simple controller while being part of a system that performs relatively complex tasks and computations.

For example, the service 1150*a* can retrieve one or more machine learning models from a remote data store and use those models to determine the advanced sleep data 1114. The service 1150*a* can retrieve one or more models to determine overall sleep quality of the user based on currently detected sensor data 1112 and/or historic sensor data. The service 1150*a* can retrieve other models to determine whether the user is snoring based on the detected sensor data 1112. The service 1150*a* can retrieve other models to determine whether the user experiences a health condition based on the data 1112.

Figure 12:
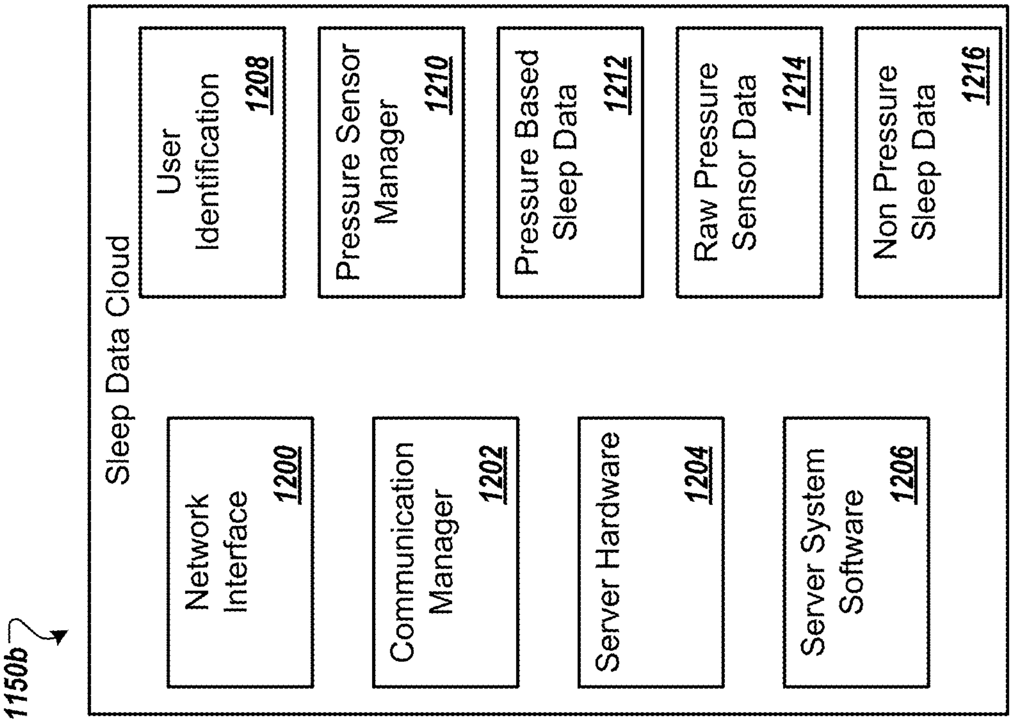
FIGS. 11-13 are block diagrams of example cloud services that can be used in a data processing system associated with a bed system.

FIG. 12 is a block diagram of an example sleep data cloud service 1150*b* used in a data processing system associated with a bed system. Here, the sleep data cloud service 1150*b* is configured to record data related to users' sleep experience. The service 1150*b* includes a network interface 1200, a communication manager 1202, server hardware 1204, and server system software 1206. The service 1150*b* also includes a user identification module 1208, a pressure sensor manager 1210, a pressure based sleep data module 1212, a raw pressure sensor data module 1214, and a non-pressure sleep data module 1216. Sometimes, the service 1150*b* can include a sensor manager for each sensor. The service 1150*b* can also include a sensor manager that relates to multiple sensors in beds (e.g., a single sensor manager can relate to pressure, temperature, light, movement, and audio sensors in a bed).

The pressure sensor manager 1210 can include, or reference, data related to the configuration and operation of pressure sensors in beds. This data can include an identifier of the types of sensors in a particular bed, their settings and calibration data, etc. The pressure based sleep data 1212 can use raw pressure sensor data 1214 to calculate sleep metrics tied to pressure sensor data. For example, user presence, movements, weight change, heartrate, and breathing rate can be determined from raw pressure sensor data 1214. An index or indexes stored by the service 1150*b* can identify users associated with pressure sensors, raw pressure sensor data, and/or pressure based sleep data. The non-pressure sleep data 1216 can use other sources of data to calculate sleep metrics. User-entered preferences, light sensor readings, and sound sensor readings can be used to track sleep data. User presence can also be determined from a combination of raw pressure sensor data 1214 and non-pressure sleep data 1216 (e.g., raw temperature data). Sometimes, bed presence can be determined using only the temperature data. Changes in temperature data can be monitored to determine bed presence or absence in a temporal interval (e.g., window of time) of a given duration. The temperature and/or pressure data can also be combined with other sensing modalities or motion sensors that reflect different forms of movement (e.g., load cells) to accurately detect user presence. For example, the temperature and/or pressure data can be provided as input to a bed presence classifier, which can determine user bed presence based on real-time or near real-time data collected at the bed. The classifier can be trained to differentiate the temperature data from the pressure data, identify peak values in the temperature and pressure data, and generate a bed presence indication based on correlating the peak values. The peak values can be within a threshold distance from each other to then generate an indication that the user is in the bed. An index or indexes stored by the service 1150*b* can identify users associated with sensors and/or the data 1216.

Figure 13:
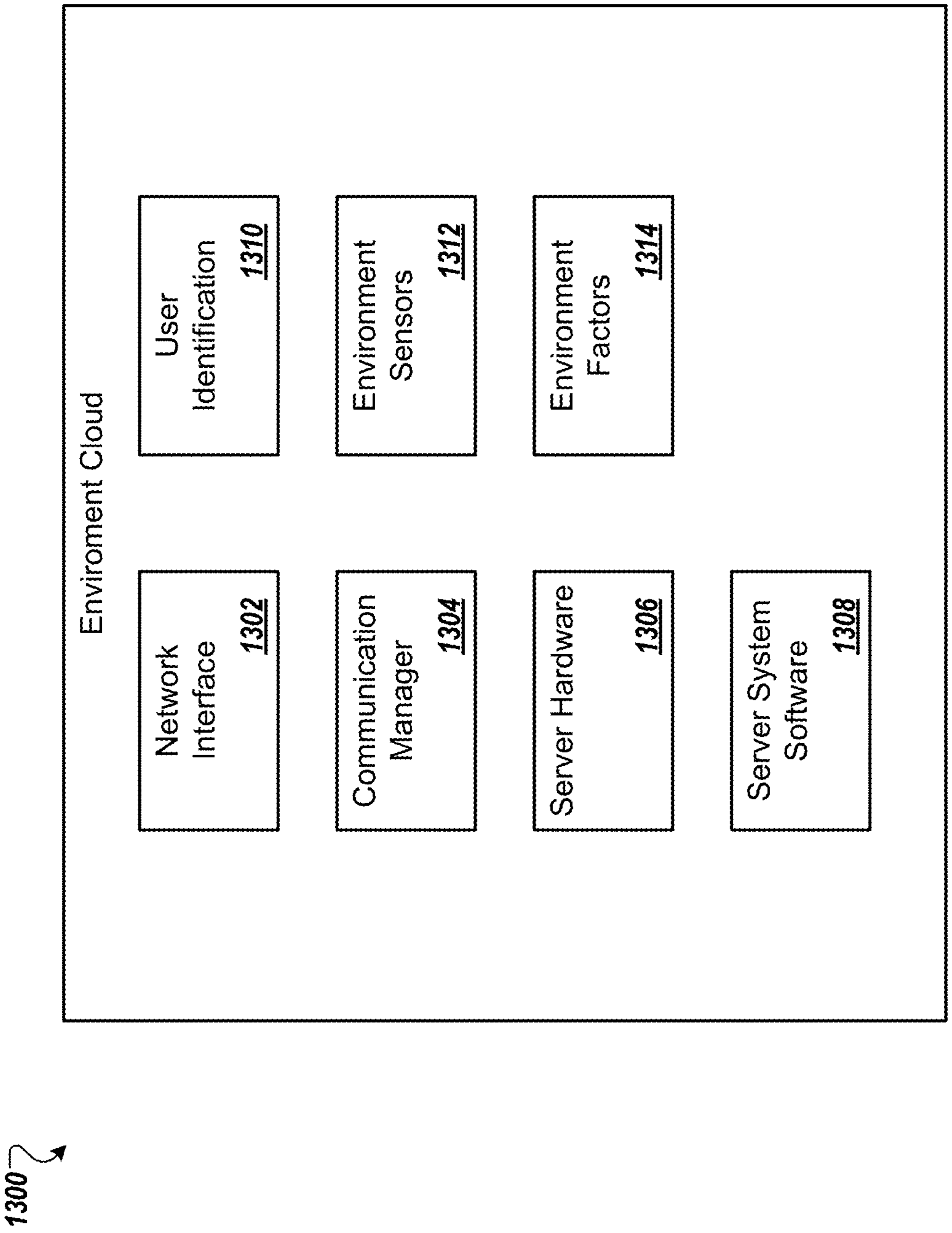

FIG. 13 is a block diagram of an example environment cloud service 1300 used in a data processing system associated with a bed system. Here, the service 1300 is configured to record data related to users' home environment. The service 1300 includes a network interface 1302, a communication manager 1304, server hardware 1306, and server system software 1308. The service 1300 also includes a user identification module 1310, an environmental sensors module 1312, and an environmental factors module 1314. The environmental sensors module 1312 can include a listing and identification of sensors that users identified in the module 1310 to have installed in and/or surrounding their bed (e.g., light, noise/audio, vibration, thermostats, movement/motion sensors). The module 1312 can also store historical readings or reports from the environmental sensors. The module 1312 can be accessed at a later time and used by one or more cloud services described herein to determine sleep quality and/or health information of the users. The environmental factors module 1314 can include reports generated based on data in the module 1312. For example, the module 1314 can generate and retain a report indicating frequency and duration of instances of increased lighting when the user is asleep based on light sensor data that is stored in the environment sensors module 1312.

In the examples discussed here, each cloud service 1150 is shown with some of the same components. These same components can be partially or wholly shared between services, or they can be separate. Sometimes, each service can have separate copies of some or all the components that are the same or different in some ways. These components are provided as illustrative examples. In other examples, each cloud service can have different number, types, and styles of components that are technically possible.

Figure 14:
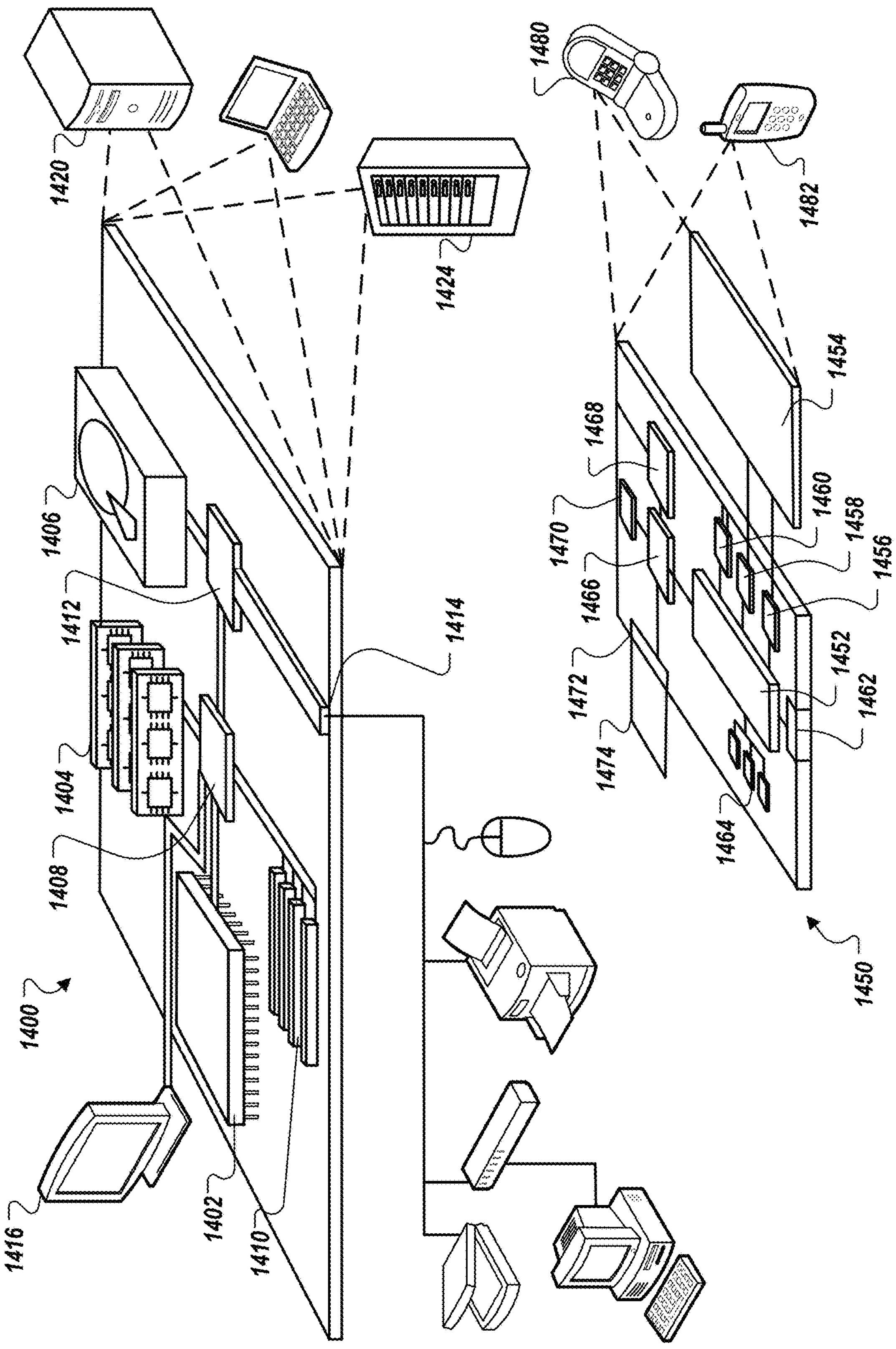
FIG. 14 is a schematic diagram that shows an example of a computing device and a mobile computing device.

FIG. 14 shows an example of a computing device 1400 and an example of a mobile computing device that can be used to implement the techniques described here. The computing device 1400 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 1400 includes a processor 1402, a memory 1404, a storage device 1406, a high-speed interface 1408 connecting to the memory 1404 and multiple high-speed expansion ports 1410, and a low-speed interface 1412 connecting to a low-speed expansion port 1414 and the storage device 1406. Each of the processor 1402, the memory 1404, the storage device 1406, the high-speed interface 1408, the high-speed expansion ports 1410, and the low-speed interface 1412, are interconnected using various busses, and can be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as a display 1416 coupled to the high-speed interface 1408. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 1404 stores information within the computing device 1400. In some implementations, the memory 1404 is a volatile memory unit or units. In some implementations, the memory 1404 is a non-volatile memory unit or units. The memory 1404 can also be another form of computer-readable medium, such as a magnetic or optical disk.

The storage device 1406 is capable of providing mass storage for the computing device 1400. In some implementations, the storage device 1406 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 1404, the storage device 1406, or memory on the processor 1402.

The high-speed interface 1408 manages bandwidth-intensive operations for the computing device 1400, while the low-speed interface 1412 manages lower bandwidth-intensive operations. Such allocation of functions is exemplary only. In some implementations, the high-speed interface 1408 is coupled to the memory 1404, the display 1416 (e.g., through a graphics processor or accelerator), and to the high-speed expansion ports 1410, which can accept various expansion cards (not shown). In the implementation, the low-speed interface 1412 is coupled to the storage device 1406 and the low-speed expansion port 1414. The low-speed expansion port 1414, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 1400 can be implemented in a number of different forms, as shown in the figure. For example, it can be implemented as a standard server 1420, or multiple times in a group of such servers. In addition, it can be implemented in a personal computer such as a laptop computer 1422. It can also be implemented as part of a rack server system 1424. Alternatively, components from the computing device 1400 can be combined with other components in a mobile device (not shown), such as a mobile computing device 1450. Each of such devices can contain one or more of the computing device 1400 and the mobile computing device 1450, and an entire system can be made up of multiple computing devices communicating with each other.

The mobile computing device 1450 includes a processor 1452, a memory 1464, an input/output device such as a display 1454, a communication interface 1466, and a transceiver 1468, among other components. The mobile computing device 1450 can also be provided with a storage device, such as a micro-drive or other device, to provide additional storage. Each of the processor 1452, the memory 1464, the display 1454, the communication interface 1466, and the transceiver 1468, are interconnected using various buses, and several of the components can be mounted on a common motherboard or in other manners as appropriate.

The processor 1452 can execute instructions within the mobile computing device 1450, including instructions stored in the memory 1464. The processor 1452 can be implemented as a chipset of chips that include separate and multiple analog and digital processors. The processor 1452 can provide, for example, for coordination of the other components of the mobile computing device 1450, such as control of user interfaces, applications run by the mobile computing device 1450, and wireless communication by the mobile computing device 1450.

The processor 1452 can communicate with a user through a control interface 1458 and a display interface 1456 coupled to the display 1454. The display 1454 can be, for example, a TFT (Thin-Film-Transistor Liquid Crystal Display) display or an OLED (Organic Light Emitting Diode) display, or other appropriate display technology. The display interface 1456 can comprise appropriate circuitry for driving the display 1454 to present graphical and other information to a user. The control interface 1458 can receive commands from a user and convert them for submission to the processor 1452. In addition, an external interface 1462 can provide communication with the processor 1452, so as to enable near area communication of the mobile computing device 1450 with other devices. The external interface 1462 can provide, for example, for wired communication in some implementations, or for wireless communication in other implementations, and multiple interfaces can also be used.

The memory 1464 stores information within the mobile computing device 1450. The memory 1464 can be implemented as one or more of a computer-readable medium or media, a volatile memory unit or units, or a non-volatile memory unit or units. An expansion memory 1474 can also be provided and connected to the mobile computing device 1450 through an expansion interface 1472, which can include, for example, a SIMM (Single In Line Memory Module) card interface. The expansion memory 1474 can provide extra storage space for the mobile computing device 1450, or can also store applications or other information for the mobile computing device 1450. Specifically, the expansion memory 1474 can include instructions to carry out or supplement the processes described above, and can include secure information also. Thus, for example, the expansion memory 1474 can be provide as a security module for the mobile computing device 1450, and can be programmed with instructions that permit secure use of the mobile computing device 1450. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 1464, the expansion memory 1474, or memory on the processor 1452. In some implementations, the computer program product can be received in a propagated signal, for example, over the transceiver 1468 or the external interface 1462.

The mobile computing device 1450 can communicate wirelessly through the communication interface 1466, which can include digital signal processing circuitry where necessary. The communication interface 1466 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 1468 using a radio-frequency. In addition, short-range communication can occur, such as using a Bluetooth, WiFi, or other such transceiver (not shown). In addition, a GPS (Global Positioning System) receiver module 1470 can provide additional navigation- and location-related wireless data to the mobile computing device 1450, which can be used as appropriate by applications running on the mobile computing device 1450.

The mobile computing device 1450 can also communicate audibly using an audio codec 1460, which can receive spoken information from a user and convert it to usable digital information. The audio codec 1460 can likewise generate audible sound for a user, such as through a speaker, e.g., in a handset of the mobile computing device 1450. Such sound can include sound from voice telephone calls, can include recorded sound (e.g., voice messages, music files, etc.) and can also include sound generated by applications operating on the mobile computing device 1450.

The mobile computing device 1450 can be implemented in a number of different forms, as shown in the figure. For example, it can be implemented as a cellular telephone 1480. It can also be implemented as part of a smart-phone 1482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

What is claimed is:

1. A system for generating sleeper information based on user data collected at a bed system, the system comprising:

a bed system including:

at least one sensor configured to generate sensor signals as a user rests on the bed system, and an edge computing device in communication over a network with other components of the bed system;

a plurality of service-providing servers each having one or more processors and memory, wherein the plurality of service-providing servers is in communication over the network with the other components of the bed system, wherein each of the plurality of service-providing servers is configured to execute a model for determining particular sleeper information based at least in part on the sensor signals generated by the at least one sensor, wherein a first subset of the plurality of service-providing servers run in a cloud-based system and a second subset of the plurality of service-providing servers run at the edge computing device; and a cloud-based computing system having one or more processors and memory, the cloud-based computing system including:

(i) a messaging service configured to provide communication over the network between the cloud-based computing system, the at least one sensor, the edge computing device, and the plurality of service-providing servers, wherein the messaging service is further configured to:

receive the generated sensor signals from the at least one sensor; and transmit the received sensor signals to a data store for storage;

(ii) a model wrapping service configured to:

receive, from a service-providing server amongst the plurality of service-providing servers via the messaging service, a request to execute a model that has a relationship with the service-providing server;

retrieve, from the data store via the messaging service, the model and data for executing the model at the requesting service-providing server, wherein the data includes at least some of the sensor signals;

wrap the model with the retrieved data; and transmit, via the messaging service, the wrapped model and data to the service-providing server for execution; and (iii) an aggregator that is configured to:

receive, from the service-providing server via the messaging service, model output once the wrapped model is executed by the service-providing server; and generate at least one health metric about the user of the bed system based on correlating the model output with at least one of (i) other model outputs or (ii) other data about the user.

2. The system of claim 1, wherein the first subset of the plurality of service-providing servers includes an illness detection service-providing server, the illness detection service-providing server being configured to execute an illness detection model having been trained to determine, over a threshold quantity of sleep sessions of the user, whether the user developed an illness, wherein the illness detection model is trained to receive, as inputs, historic user health data, the generated sensor signals, and model output from one or more of the plurality of service-providing servers, process the received inputs, and generate, as a result of processing the inputs, output indicating a likelihood that the user developed the illness.

3. The system of claim 1, wherein the second subset of the plurality of service-providing servers includes: a motion detection service-providing server, a respiratory rate detection service-providing server, a heartrate detection service-providing server, a heartrate variability computation service-providing server, a time-to-fall-asleep computation service-providing server, a bed presence detection service-providing server, a snore detection service-providing server, and a snore response service-providing server.

4. The system of claim 1, wherein the at least one health metric is a determination of the user's vitals at one or more time intervals during a sleep session of the user.

5. The system of claim 1, wherein the at least one health metric is generated using one or more rules for correlating different types of model outputs to determine the health metric.

6. The system of claim 1, wherein the at least one health metric is generated using a model having been trained to correlate different types of model outputs to determine the health metric.

7. The system of claim 1, wherein the plurality of service-providing servers includes a snore detection service-providing server, the snore detection service-providing server being part of the second subset of the plurality of service-providing servers run at the edge computing device, wherein the snore detection service-providing server is configured to:

receive, from an acoustic sensor of the bed system, acoustic signals while the user rests on the bed system;

pass the acoustic signals to a snore detection model that is executed at the snore detection service-providing server and configured to generate output indicating whether the user snores while the user rests on the bed system; and transmit the snore detection model output to the messaging service of the cloud-based computing system for further processing.

8. The system of claim 7, wherein the plurality of service-providing servers includes a sleep stage service-providing server, the sleep stage service-providing server being part of the first subset of the plurality of service-providing servers run at the cloud-based computing system, wherein the sleep stage service-providing server is configured to:

receive, from a pressure sensor of the bed system, pressure signals while the user rests on the bed system;

pass the pressure signals to a sleep stage model that is executed at the sleep stage service-providing server and configured to generate output indicating at least heartrate of the user at predetermined time intervals while the user rests on the bed system; and transmit the sleep stage model output to the messaging service of the cloud-based computing system for further processing.

9. The system of claim 8, wherein the cloud-based computing system is further configured to: transmit, to the snore detection service-providing server via the messaging service, the snore detection model output and a portion of the sleep stage model output, wherein the portion of the sleep stage model output includes the predetermined time intervals, and the snore detection service-providing server is further configured to correlate identified snore detections in the snore detection model output with the predetermined time intervals to determine when the user snores while resting on the bed system.

10. The system of claim 8, wherein the cloud-based computing system is further configured to pass the snore detection model output and the sleep stage model output to the aggregator, wherein the aggregator is further configured to correlate the snore detection model output with the sleep stage model output to determine a health condition of the user.

11. The system of claim 10, wherein determining the health condition of the user comprises applying an aggregation model to the snore detection model output and the sleep stage model output, the aggregation model having been trained to correlate data and determine health conditions of users based on the correlated data.

12. The system of claim 1, wherein the cloud-based computing system further includes a model training engine, the model training engine being configured to:

receive, as training inputs to models that are executed at the plurality of service-providing servers, the generated sensor signals, model outputs, the at least one health metric, and historic data about a population of users of bed systems;

aggregate the received training inputs;

iteratively train, for each of the plurality of service-providing servers, the model that is executed by the service-providing server with a portion of the aggregated training inputs, wherein the portion of the aggregated training inputs has a relationship with the particular sleeper information determined by the model; and pass the trained model to the model wrapping service for wrapping and deployment to the service-providing server.

13. The system of claim 1, wherein the messaging service is further configured to load, based on the retrieved data, the model as a plugin and wrap the plugin model.

14. The system of claim 1, wherein the at least one sensor includes a pressure sensor and the sensor signals are pressure signals.

15. The system of claim 1, wherein the at least one sensor includes an audio sensor and the sensor signals are audio signals.

16. The system of claim 1, wherein the at least one sensor includes a temperature sensor and the sensor signals are temperature signals.

17. The system of claim 1, wherein the at least one sensor includes an array of temperature signals and the sensor signals are temperature signals.

18. The system of claim 1, wherein the at least one sensor includes a load cell and the sensor signals are load cell signals.

19. The system of claim 1, wherein the at least one sensor includes a combination of any one or more of the group comprising: pressure sensors, audio sensors, temperature sensors, and load cells.

20. The system of claim 1, wherein the edge computing device is a controller of the bed system.

* * * * *